(12) United States Patent
Benttine et al.

(10) Patent No.: US 8,223,200 B1
(45) Date of Patent: Jul. 17, 2012

(54) PACKAGE VISION EVALUATION SYSTEM

(75) Inventors: Carl Leroy Benttine, St. Ansgar, IA (US); William D. Young, Owatonna, MN (US); Nathan A. Kodesh, Austin, MN (US)

(73) Assignee: Hormel Foods Corporation, Austin, MN (US)

( * ) Notice: Subject to any disclaimer, the term of this patent is extended or adjusted under 35 U.S.C. 154(b) by 354 days.

(21) Appl. No.: 12/481,316

(22) Filed: Jun. 9, 2009

(51) Int. Cl.
*H04N 7/18* (2006.01)
(52) U.S. Cl. .......................................... 348/89; 382/143
(58) Field of Classification Search ................... 348/86, 348/89; 356/241.1, 364; 382/141, 143
See application file for complete search history.

(56) References Cited

U.S. PATENT DOCUMENTS

| | | | |
|---|---|---|---|
| 5,184,190 A | 2/1993 | Rai et al. | |
| 5,515,159 A | 5/1996 | Sites et al. | |
| 5,805,279 A | 9/1998 | Palombo et al. | |
| 5,969,810 A * | 10/1999 | Nicks et al. | 356/239.4 |
| 6,005,965 A * | 12/1999 | Tsuda et al. | 382/145 |
| 6,097,427 A | 8/2000 | Dey et al. | |
| 6,201,892 B1 | 3/2001 | Ludlow et al. | |
| 6,259,522 B1 * | 7/2001 | Her | 356/237.5 |
| 6,396,578 B2 | 5/2002 | Her | |
| 6,545,754 B2 | 4/2003 | Her | |
| 6,597,806 B1 | 7/2003 | Kawada | |
| 6,655,114 B2 | 12/2003 | Hiramoto et al. | |
| 6,744,515 B1 | 6/2004 | Totani | |
| 6,765,185 B2 | 7/2004 | Swab | |
| 7,142,707 B2 | 11/2006 | Abdollahi et al. | |
| 2003/0044056 A1 | 3/2003 | Katt et al. | |
| 2003/0161524 A1 | 8/2003 | King | |

* cited by examiner

*Primary Examiner* — Viet Vu
(74) *Attorney, Agent, or Firm* — IPLM Group, P.A.

(57) ABSTRACT

Apparatus and methods of evaluating packages are provided. In a vision evaluation system embodiment, the system includes a light source, a first and second camera and a control system. The light source provides polarized backlight. The first camera has a first lens positioned to image the polarized back light. A ninety degree polarized filter is positioned between the first lens of the first camera and the light source. The ninety degree polarized filter is polarized 90 degrees from the polarized back light of the light source. The second camera has a second lens that is positioned near the first lens of the first camera. The control system is coupled to control the first and second cameras to take simultaneous images at a given frequency. The control system is further configured to determine locations to analyze based on image data from the first camera. Moreover, the control system is still further configured to analyze the determined locations in associated image data from the second camera. Packages whose image fails the analysis are removed from a packing line.

33 Claims, 25 Drawing Sheets

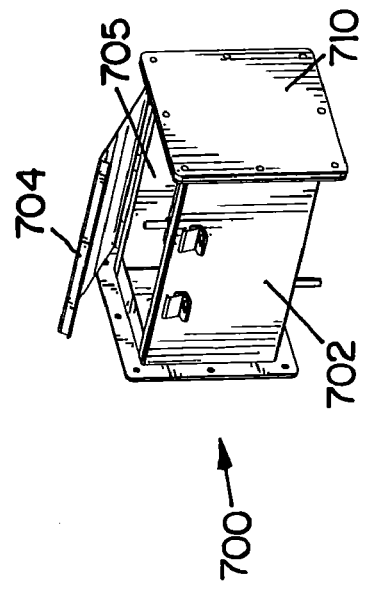
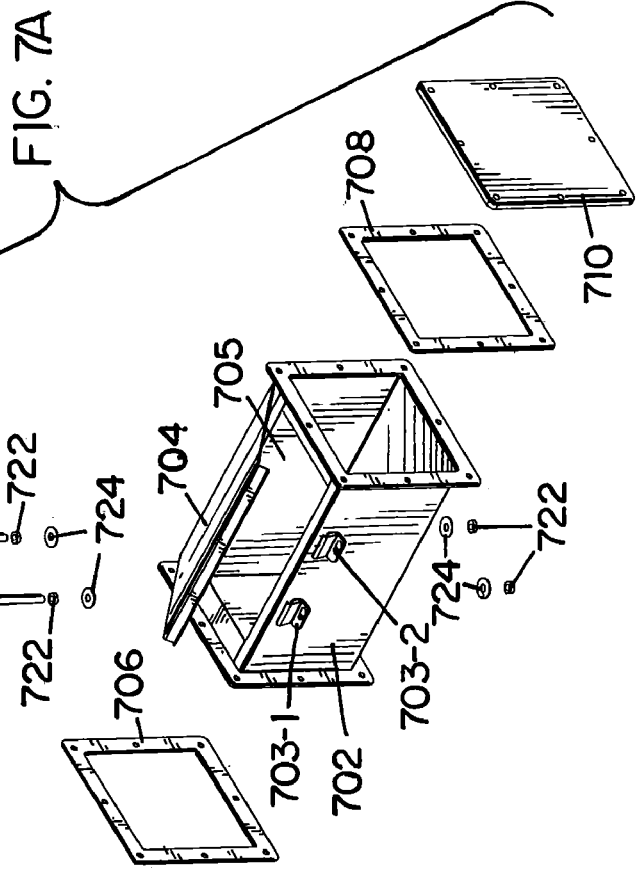
FIG. 7B
FIG. 7A

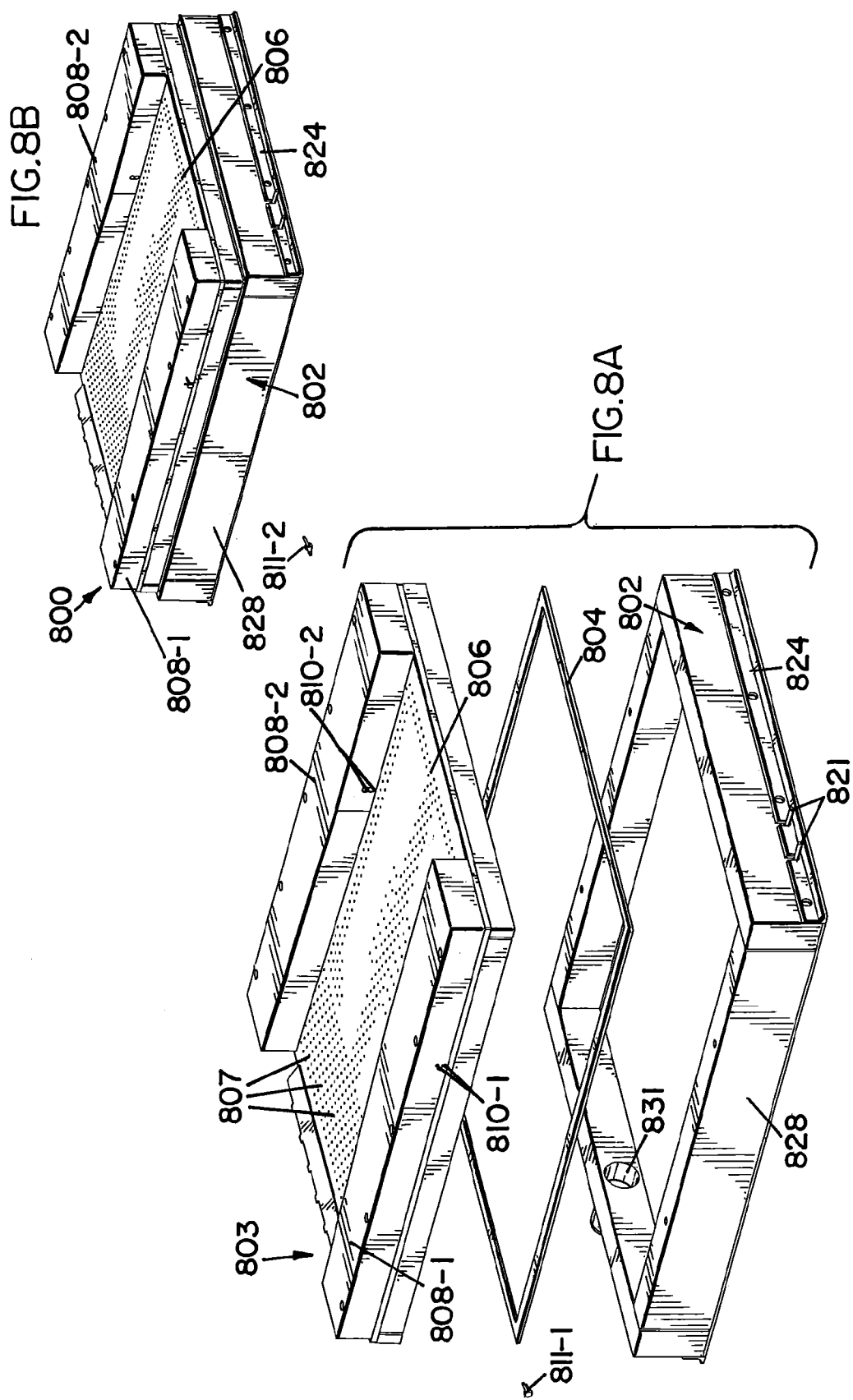

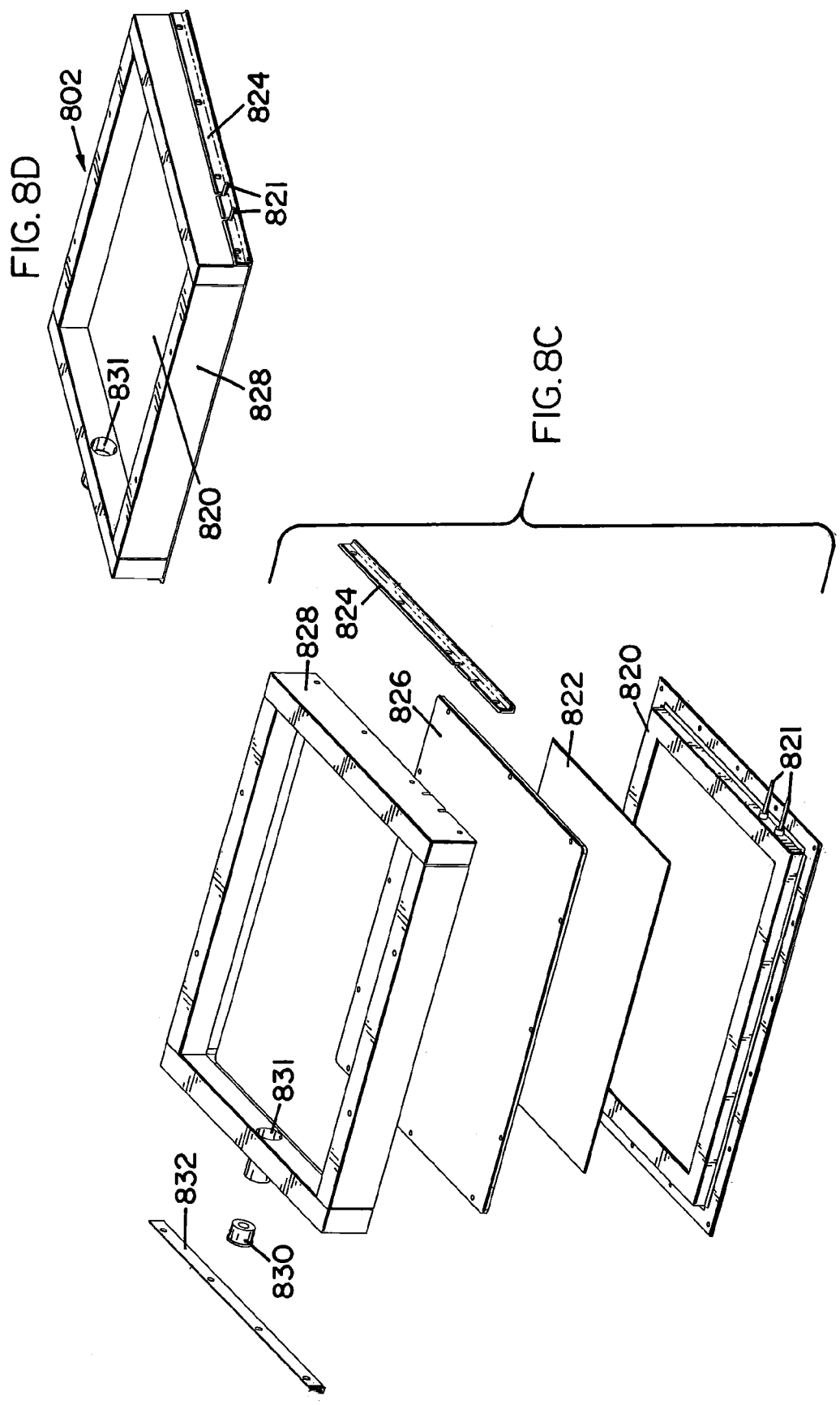

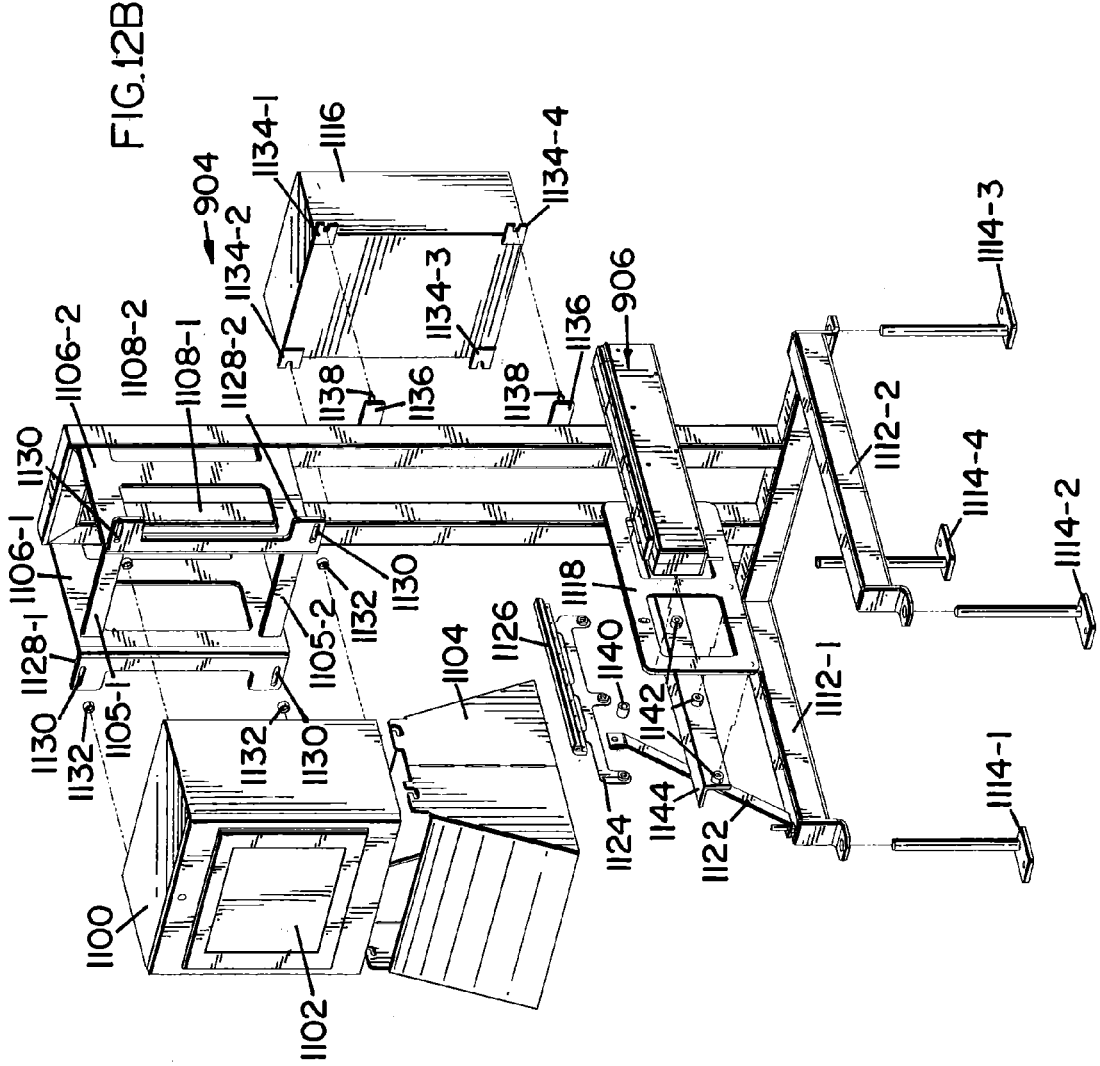

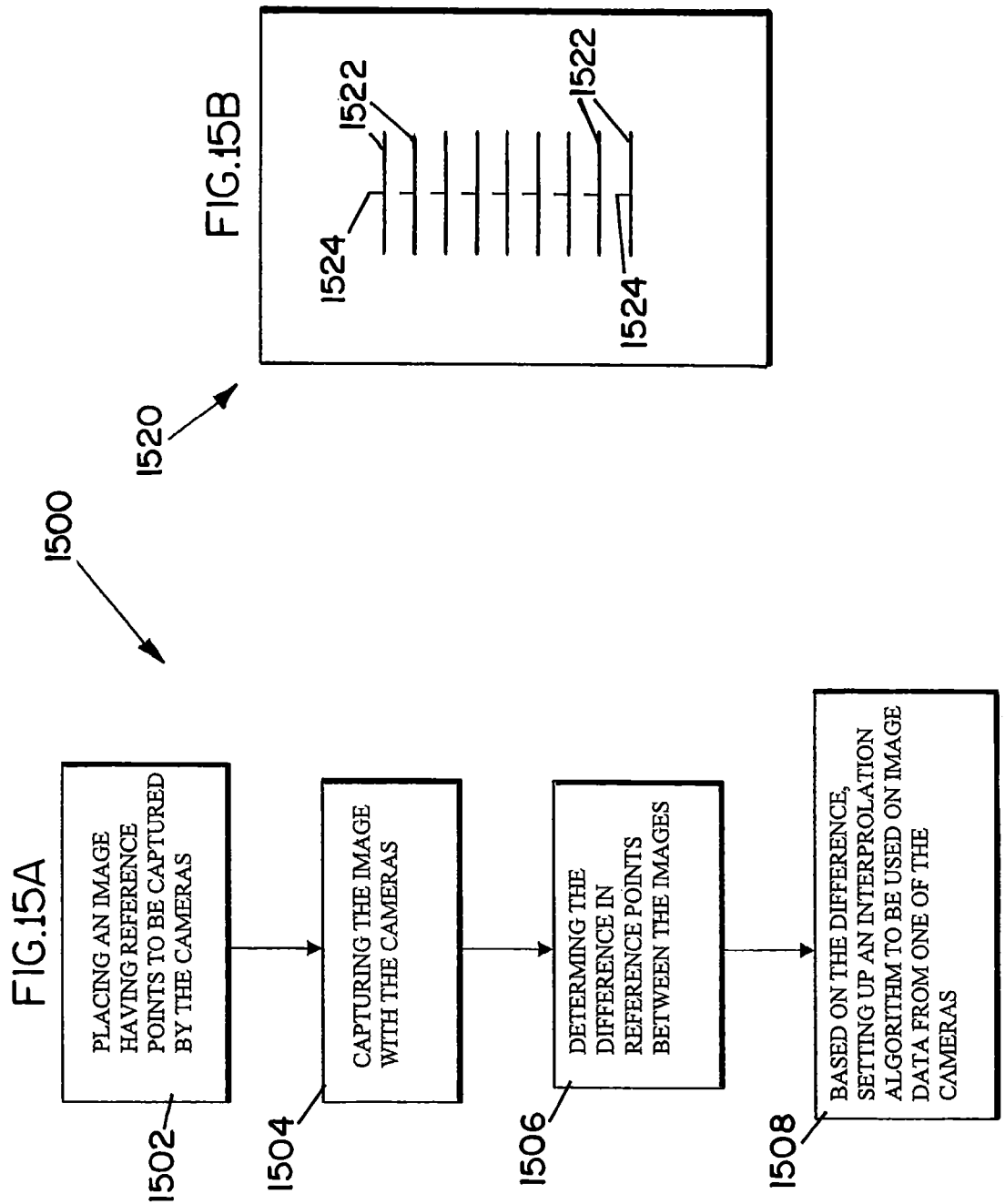

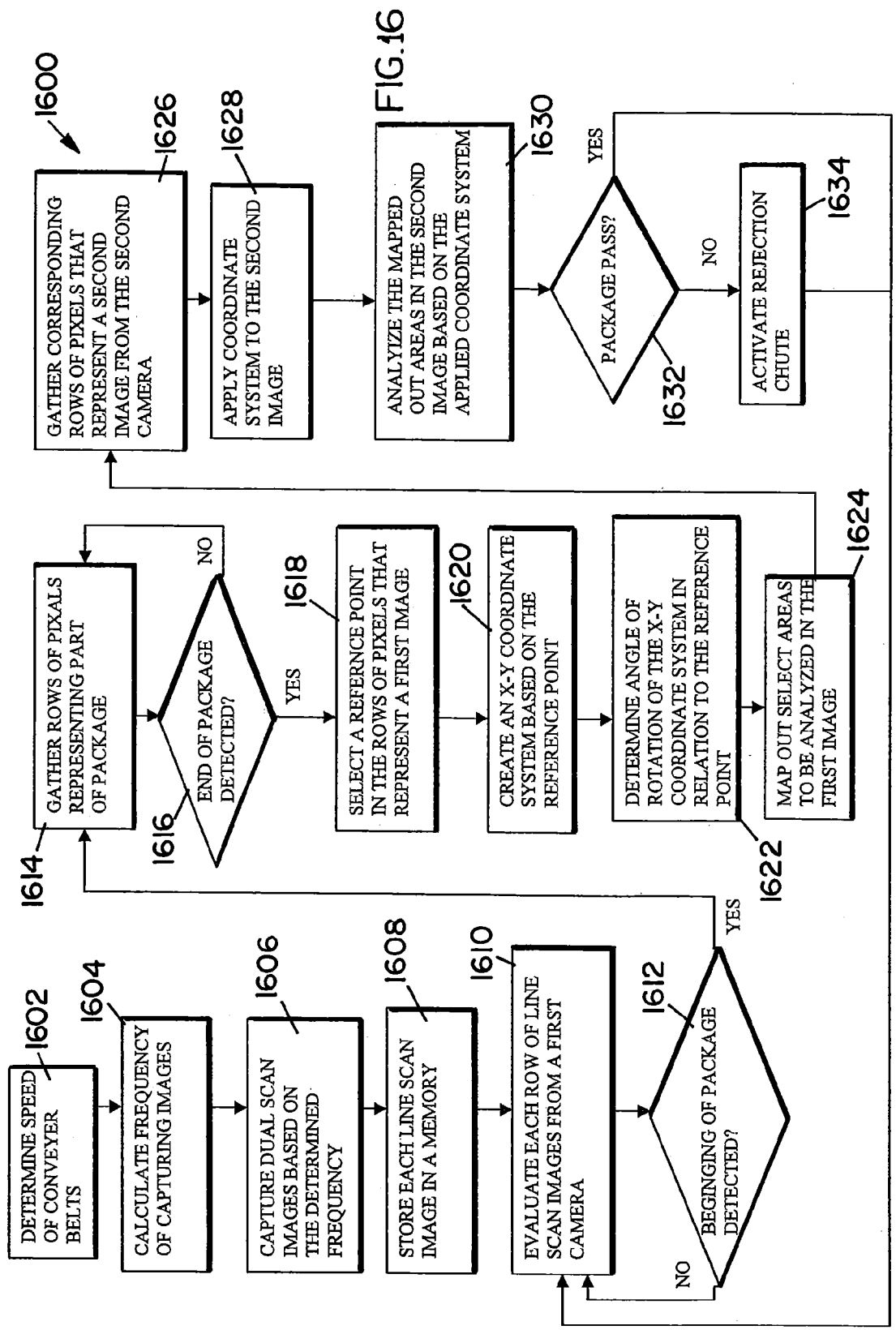

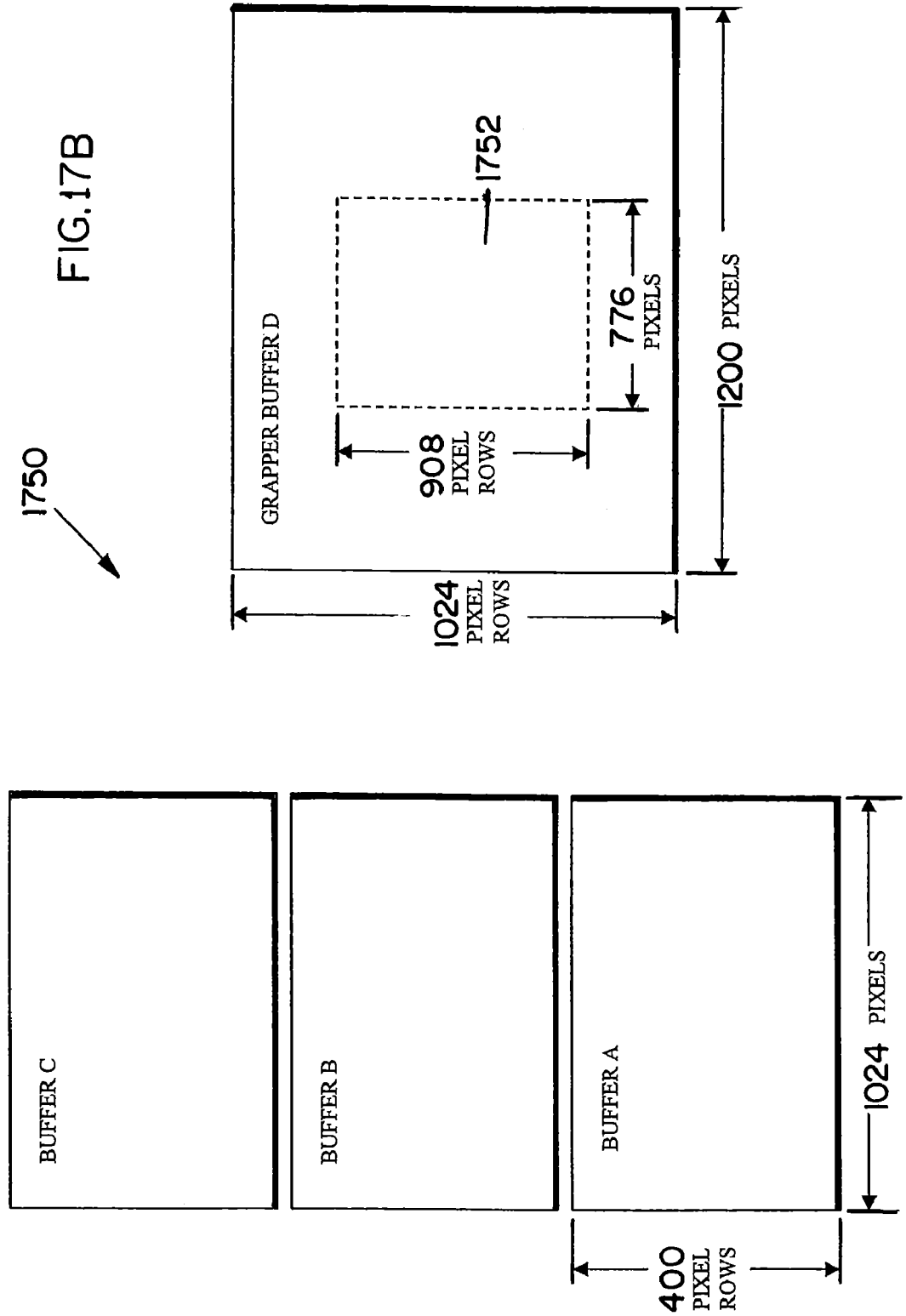

PACKAGE VISION EVALUATION SYSTEM

BACKGROUND

Automated processes that analyze products or packages are used in industry to cut down on labor cost and improve product safety. In some applications just a select area of a product or package needs to be analyzed. When just select areas need to be analyzed, it is preferable not to waste analysis resources on non-select areas. Moreover, in some applications, mistakenly analyzing non-select areas result in faulty results. However, locating the select area of the product or package to be analyzed can be a challenge. For example, in some automated systems, the product or package is placed into an analyzing area such that each product or package is orientated in a different direction than the next. For example, in food packing systems it is desired to analyze seals to make sure they provide an airtight seal. However, locating just the seal portion can be difficult in a conveyer type moving system common in the food packing industry where the orientation of each package placed in an analyzing area will vary.

For the reasons stated above and for other reasons stated below which will become apparent to those skilled in the art upon reading and understanding the present specification, there is a need in the art for an effective and efficient method and system of determining select locations of a product or package to analyze.

SUMMARY OF INVENTION

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In one embodiment, a vision evaluation system is provided. The system includes a light source, a first and second camera and a control system. The light source provides polarized back light. The first camera has a first lens configured to receive the polarized backlight. A ninety degree polarized filter is positioned between the first lens of the first camera and the light source. The ninety degree polarized filter is polarized 90 degrees from the polarized back light of the light source. The second camera has a second lens that is positioned near the first lens of the first camera. The control system is coupled to control the first and second cameras to take simultaneous images at a given frequency. The control system is further configured to determine locations to analyze based on image data from the first camera. Moreover, the control system is still further configured to analyze the determined image data in associated figures from the second camera. Packages whose image fails the analysis are removed from a packing line.

BRIEF DESCRIPTION OF THE DRAWINGS

The present invention can be more easily understood and further advantages and uses thereof more readily apparent, when considered in view of the detailed description and the following figures in which:

FIG. 7A is an exploded side perspective view of a camera system of one embodiment of the present invention;

FIG. 7B is a side perspective view of an assemble camera system of the embodiment of FIG. 7A;

FIG. 8A is an exploded side perspective view of the light box of one embodiment of the present invention;

FIG. 8B is a side perspective view of an assembled light box of the embodiment of FIG. 8A;

FIG. 8C is an exploited side perspective view of a bottom portion of a light box of one embodiment of the present invention;

FIG. 8D is a side perspective view of an assembled bottom portion of a light box of the embodiment of FIG. 8C;

FIG. 12B is an unassembled perspective view of the image assembly of FIG. 12A;

FIG. 15A illustrates a calibration flow diagram of one embodiment of the present invention;

FIG. 15B illustrates an example of a calibration image of one embodiment of the present invention;

FIG. 16 illustrates an application flow diagram of one embodiment of the present invention;

FIG. 17B illustrates buffers of one embodiment of the present invention; and

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the claims and equivalents thereof.

Figure 1:
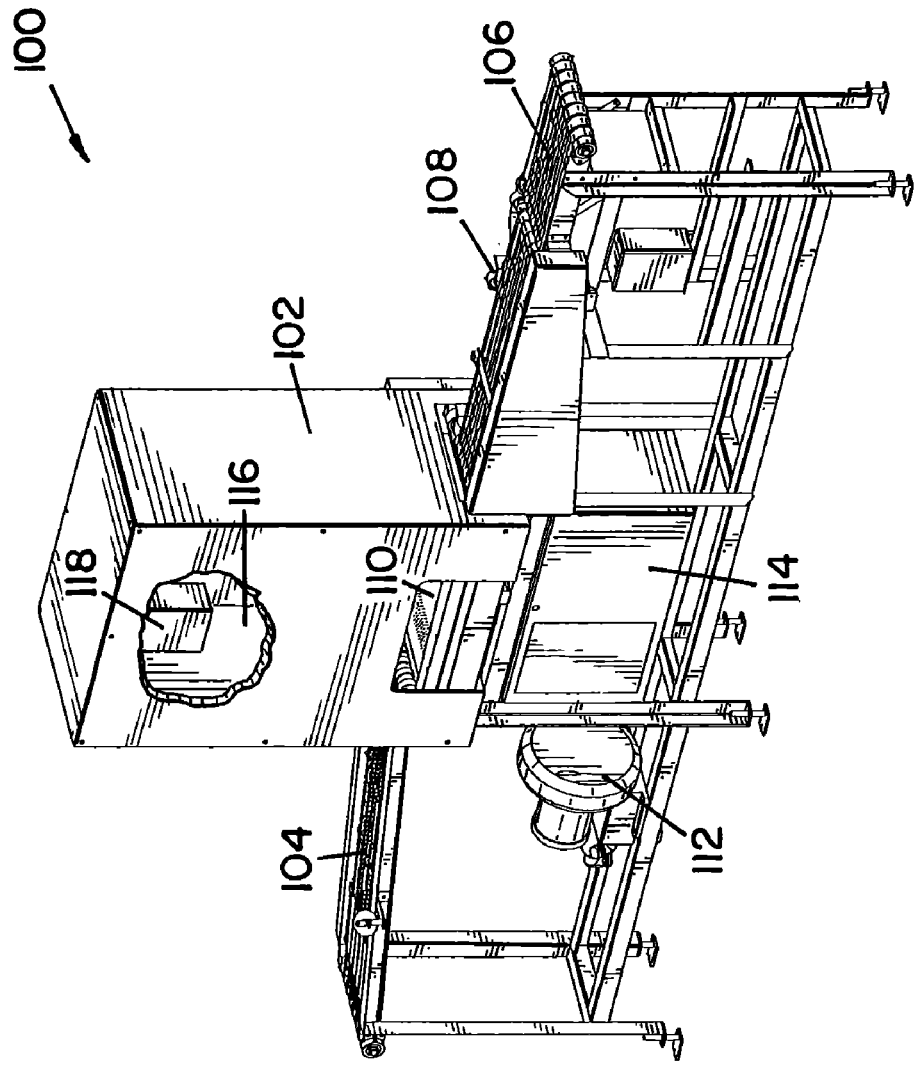
FIG. 1 is a front perspective view of vision evaluation system of one embodiment of the present invention.

Some embodiments of the present invention provide a system and method to locate select areas of an object, such as a package or product to analyze. For example, referring to FIG. 1, a package seal integrity sorting system 100 (or more generally a vision evaluation system) of one embodiment is illustrated. The evaluation system 100 includes a first conveyer 104 to bring a sealed package into an analyzing housing 102 and a second conveyer 106 to move packages from the evaluation system 100 after analysis occurs. The second conveyer includes a rejection mechanism 108 that removes packages that fail the analysis. Also illustrated in FIG. 1, is a light box 110 that is received in the housing 102. The light box 110 provides a polarized back light. The light box 110 also provides an air conveyer system that moves packages across the light box 110 in the housing 102. The air used to move the packages is supplied by fan 112. A cutaway section 116 in housing 102 in FIG. 1 illustrates a camera housing 118 mounted inside the housing 102. The camera housing 118 is further described in detail below. The camera housing 118 includes two cameras 502 and 503 (generally shown in FIG. 5) under control of a processor 506 (also generally shown in FIG. 5). The processor 506 can be generally referred to as controller. The controller 506 is located in a control housing 114. In embodiments, one of the cameras, a location camera (the first camera 502), includes a polarized filter 716 (shown in FIG. 7A) that is oriented 90 degrees from the polarized back light provided by the light box 110.

Figure 2:
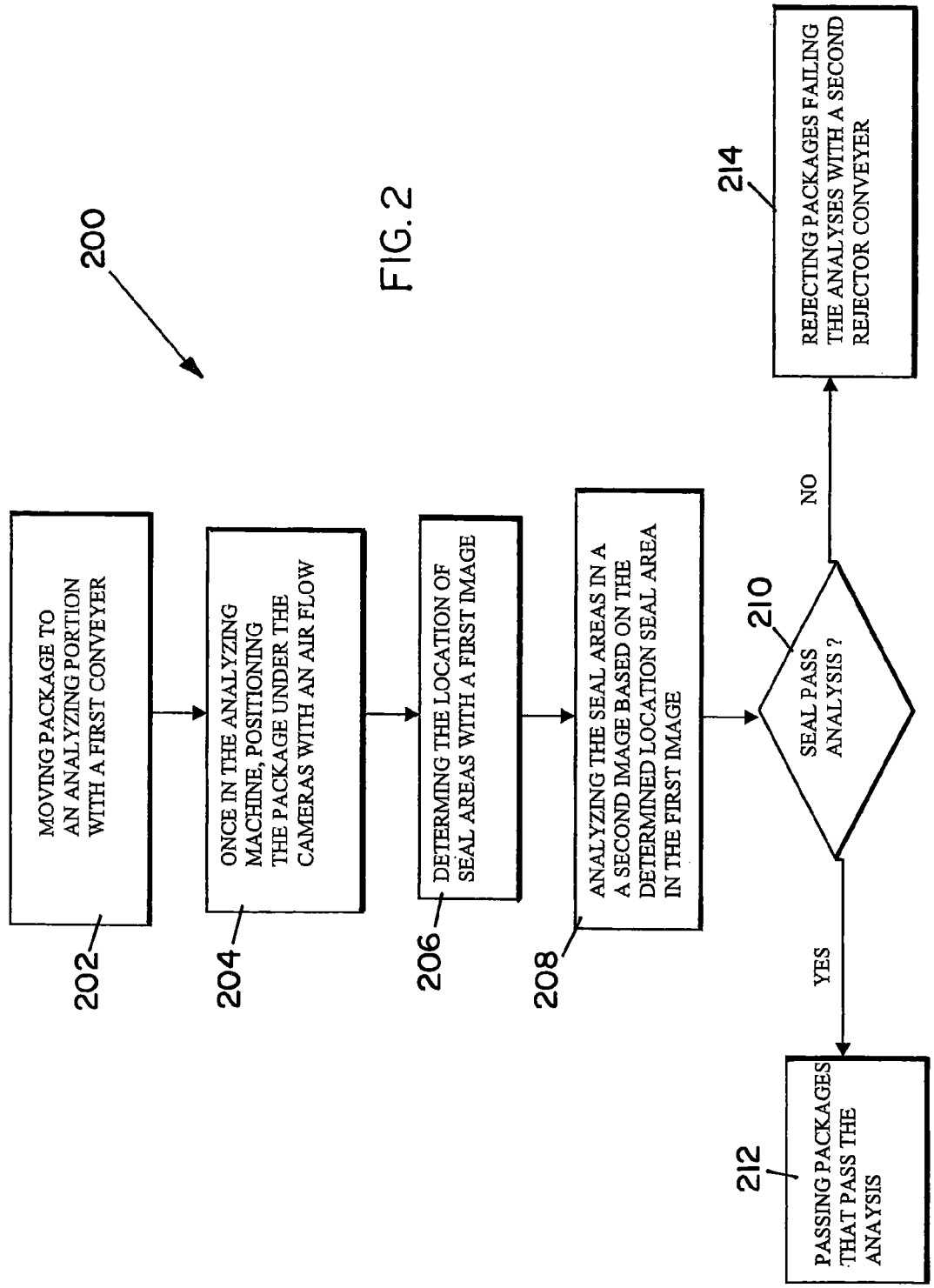
FIG. 2 is an operation flow diagram of one embodiment of the present invention.
Figure 3:
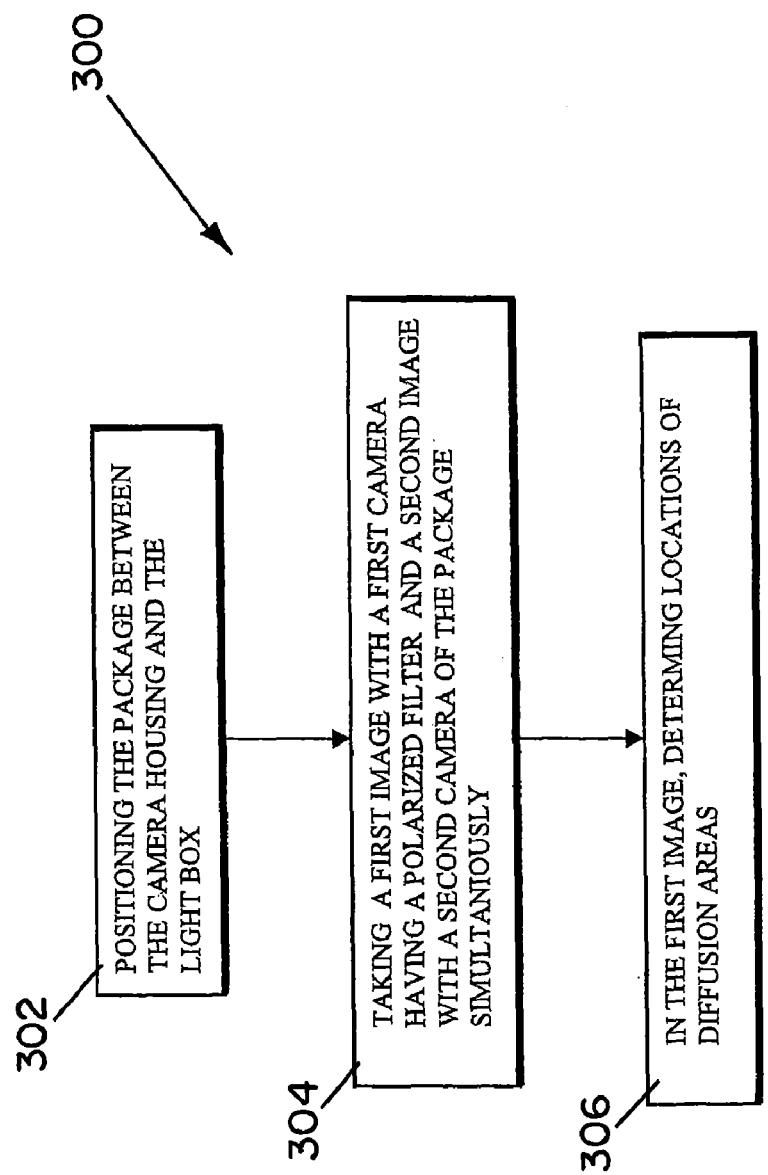
FIG. 3 is a location flow diagram of one embodiment of the present invention.
Figure 4:
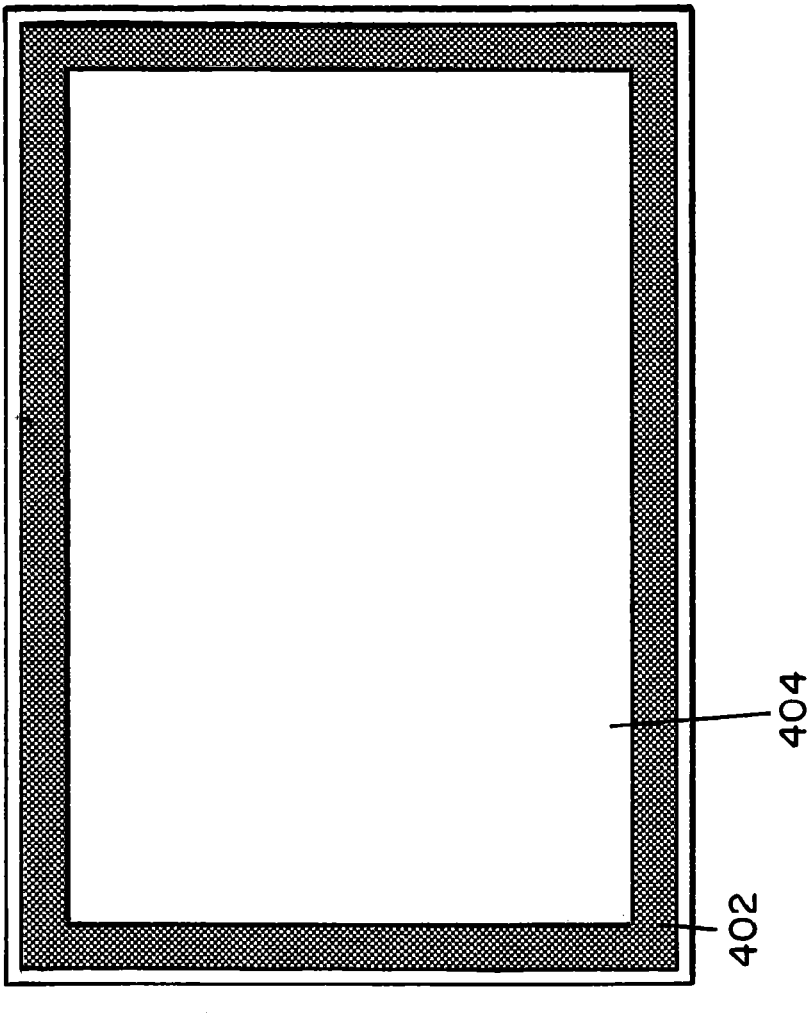
FIG. 4 is a package image example of one embodiment of the present invention.

One method of operating the package seal integrity sorting system 100 of FIG. 1 is illustrated in the operation flow diagram 200 of FIG. 2. As illustrated, the process starts by moving an object, such as a transparent sealed package, into an analyzing portion, within housing 102, of the system 100 (202). Once within the housing 102, the package is positioned under the cameras 502 and 504 (205). The positioning is done with airflow in one embodiment. The location of the seal area is first determined with a first image (206). A discussion of the location of the seal in the first image from the first camera 502 is further discussed in detail below. A second image form the second camera 504 is used to analyze the seal areas using the determined location from the first image (208). It is then determined if the seal passed the analysis (210). If the seal passed the analysis (210), the package is passed on for sale (212). If, however, the seal failed the analysis (210), the package is rejected and removed with a rejecter conveyer (214). Determining the location of the seal is further described in the location flow diagram of FIG. 3. As illustrated in FIG. 3, the package is first positioned between the camera housing 118 and the light box 110 (302). A first image and a second image are taken simultaneously with a first and second camera 502 and 504 in the camera housing 118 (304). The first camera 502 has a polarized filter 716 that is oriented 90 degrees from the polarized back light from the light box 110. Hence, the polarized back light directly from the light box will not pass through the filter of the first camera. However, polarized back light from the light box that is diffused would pass through filter of the first camera since the diffusion would change the polarization of the light. An example of a diffusion area on a transparent (plastic) package is a thermal seal area. The polarized back light from the light box will hit the thermal seal and diffuse. Some of the diffused light will enter the filter of the first camera. Therefore, the seal area will be lighter than the rest of the areas of the package in the first image. An example package image 400 taken form a first location camera with a polarized filter is illustrated in FIG. 4. In general, the area 404 that includes the product will show up darker since light cannot pass through and the thermal seal area 402 will show up lighter because of the diffusion as discussed above. Hence, the location of the seal in the first image can easily be identified.

Figure 5:
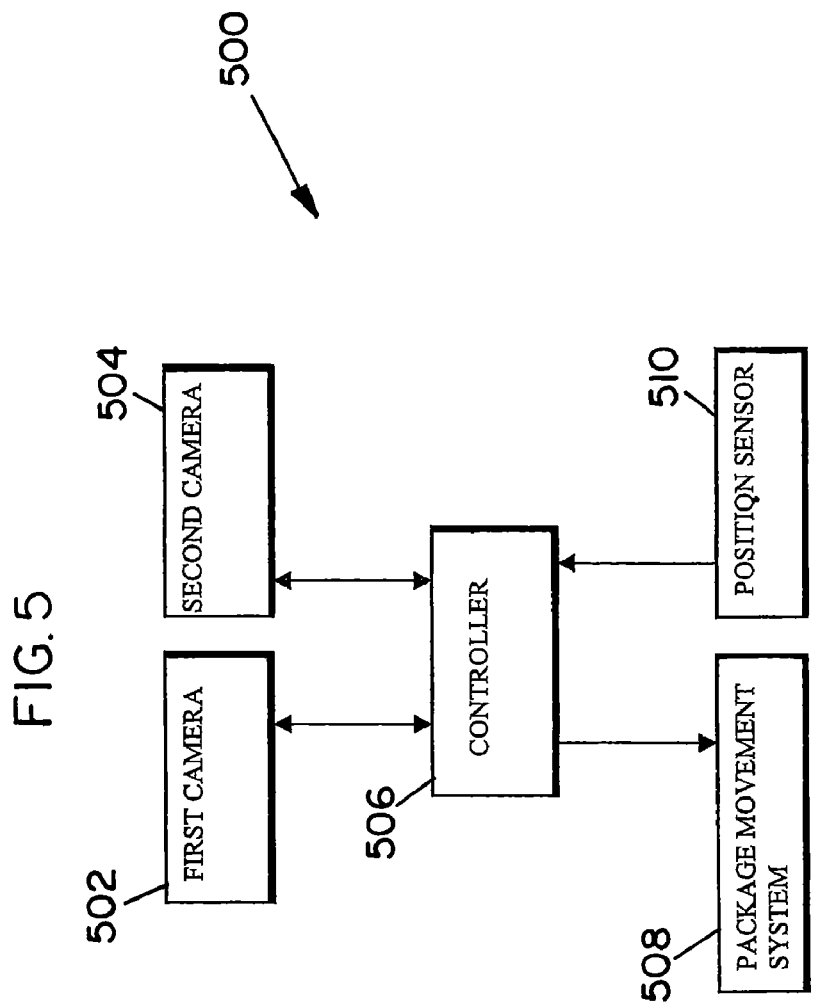
FIG. 5 is a block diagram of a package analyzing system of one embodiment of the present invention.

FIG. 5 illustrates a block diagram of a package analyzing system 500 of one embodiment of the present invention. As illustrated, the system 500 includes the first and second camera 502 and 504, a package movement system 508 and a position sensor 510 which are all controlled by the controller 506. The controller in the embodiment of FIG. 1 would be located in the control housing 114. The controller 506 controls the package movement system 508 to position the package in view of lenses of the cameras 502 and 504. In the embodiment of FIG. 1, the package movement system includes conveyer 104, 106 and an air system of the light box 110. A position sensor 510 is used by the controller 506 to determine when a package is in position to take the images. In embodiments, the first camera 502 and the second camera 504 are located in close proximity to each other so that they image basically the same area that includes the package from the same perspective. The controller 506 directs the cameras 502 and 504 to take images of a package simultaneously. As discussed above, the controller 500 then uses the first image to determine the location of the seal and then conducts an analysis on the seal with the second image. Hence, the second camera 504 that takes the second image can generally be referred to as the analyzing camera.

Figure 6:
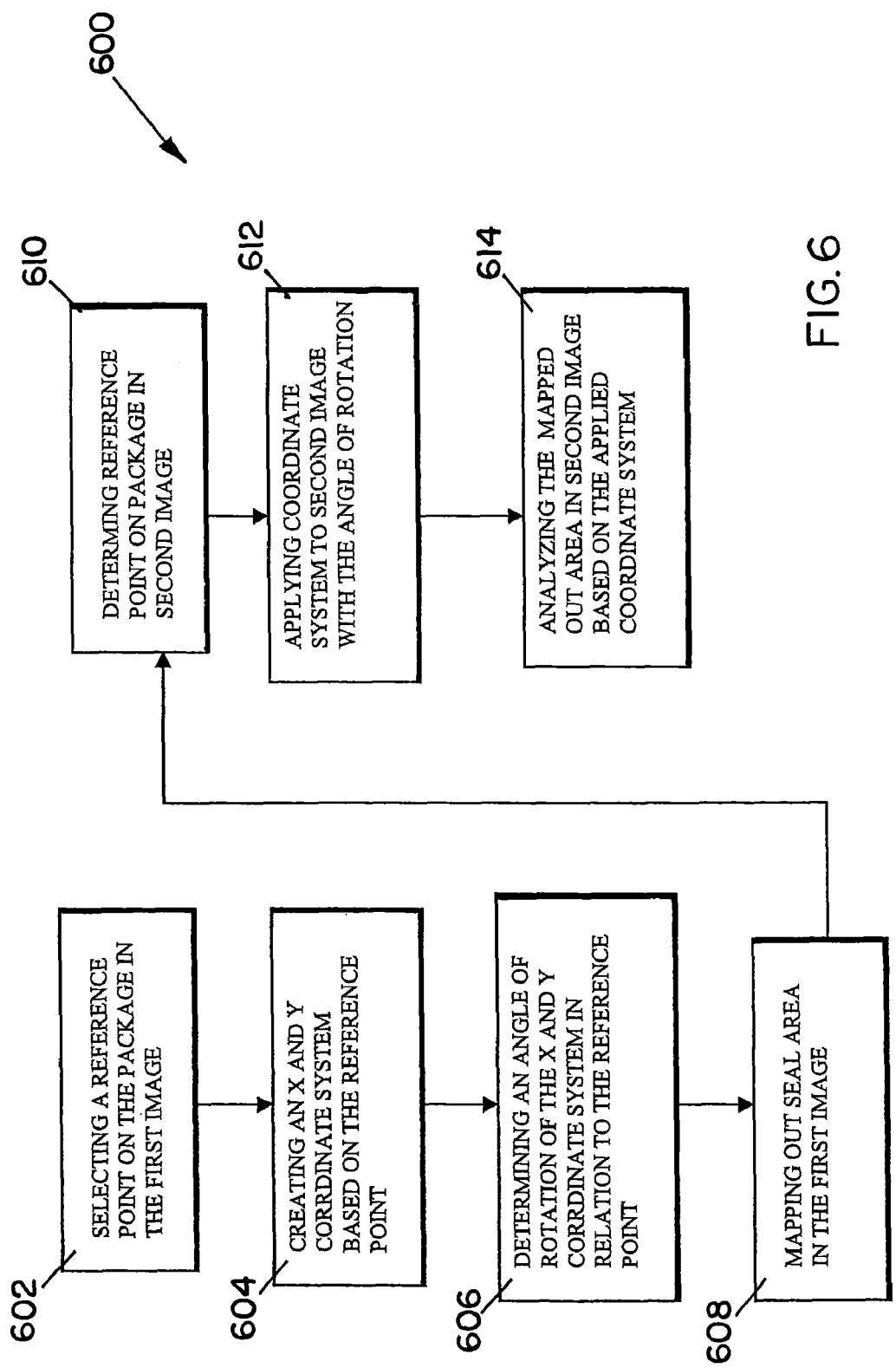
FIG. 6 is a location determination flow diagram of one embodiment of the present invention.

Referring to FIG. 6, a location determination flow diagram 600 of one embodiment is illustrated. In particular, the flow diagram 600 of FIG. 6 illustrates one method of mapping out the location of the seal with the first image and how that information is used with the second image in one embodiment. As illustrated, a reference point is selected in the first image (602). In one embodiment, the reference point is a corner of the package. Based on the reference point, a two dimensional X-Y coordinate system is created (604). An angle of rotation of the X-Y coordinate system in relation to the reference point is also determined (606). The angle of rotation is applied to the X-Y coordinate system to determine the angle orientation of the package. The area of the seal is then mapped out with the coordinate system in the first image (608). As discussed above, the seal area will show up as a lighter area because of the diffusion at the seal. The reference point is then determined on the second image (610). Since the second image was taken at the same time and from basically the same perspective, the package image location in the second image will be in the same location as it is in the first image. The X-Y coordinate system is then applied to the second image taking into account the angle of rotation (612). The mapped area of the seal is then analyzed in the second image (614). One method of analyzing the seal in the second image includes a pixel analysis. In one embodiment pixel analysis involves reviewing percentages relating to proximate pixels that are either dark or light. Other types of analyzing are contemplated.

FIGS. 7A and 7B illustrate a camera system 700 of one embodiment that takes the first and second images. In particular, FIG. 7A is an unassembled side-perspective view of camera system 700 of FIG. 7A. As illustrated, camera system 700 includes a camera housing 702 (such as camera housing 118 of FIG. 1). The camera housing 702 of this embodiment includes an access door 704 that is retained shut with retaining clips 703-1 and 703-2. The camera housing 702 forms a cavity 705 in which a first and second camera 714-1 and 714-2 are mounted. In particular, in this embodiment, cameras 714-1 and 714-2 are mounted in the camera housing 702 via rods 720, mounting plate 718, nuts 722 and washers 724. The first and second cameras 502 and 504 are illustrated with their respective lens 714-1 and 714-2. The first camera 502 (or location camera) has a polarized filter 716 mounted on its lens 714-1. A first gasket 706 is used to create a water proof seal when the camera housing 702 is mounted in an analyzing housing such as analyzing housing 102 illustrated in FIG. 1. As further illustrated, in FIGS. 7A and 7B, a transparent cover 710 is mounted on camera housing 702. A gasket 708 is positioned between the transparent cover 710 and the camera housing 702 to provide a water proof seal. Hence in embodiments of the present invention, an analyzing housing, such as analyzing housing 102 of FIG. 1, can easily be cleaned without removing the cameras 502 and 504.

FIGS. 8A and 8B illustrate a light box 800 of one embodiment. In particular, FIG. 8B illustrates a side perspective view of an assembled light box 800 and FIG. 8A illustrates an unassembled side perspective view of the light box 800. Light box 800 includes a top portion 803 and a bottom portion 802. The top portion 803 includes a pair of guide rails 808-1 and 808-2 and a transparent top panel 806. The transparent top panel 806 has a plurality of air passages 807 that allow an air flow to move a package across a surface of the transparent top panel 806. Guide rails 802-1 and 802-2 guide the package along the surface of the transparent top panel 806. Position sensors 811-1 and 811-2 fit in respective sensor apertures 810-1 and 810-2. The position sensors 811-1and 811-2 sense the presence of a package. A controller, such as controller 506 of FIG. 5, is in communication with the sensor. In embodiments, when the controller gets a signal from the sensor it activates the cameras as discussed above. In one embodiment, the sensors are fiber optic sensors 811-1 and 811-2 that detect when a package is between them. As illustrated, a gasket 4 is positioned between the top portion 803 of the air box 800 and the bottom portion 802 of the air box 800 to create an air seal.

The bottom portion 802 of the air box is further illustrated in FIGS. 8C and 8D. In particular, FIG. 8B illustrates a side perspective view of an assembled bottom portion 802 and FIG. 8C illustrates an unassembled side perspective view of a bottom portion 802. As illustrated, the bottom portion includes a light 820 having power source connectors 821. A polarized film 822 is then positioned between the light 820 and a transparent bottom panel 826. As illustrated, a light box frame 828 is coupled to the transparent bottom panel 826. Frame 828 includes an air inlet 831 that would be coupled to a fan, such as fan 112 of FIG. 1. An air flow plug 830 is received in the air inlet 831 to regulate the flow of air. Also illustrated in FIG. 8C are angle mount brackets 832 and 824 that are used to mount the light box 800 in a package seal integrity sorting system such as the package seal integrity sorting system 100 of FIG. 1.

Figure 9:
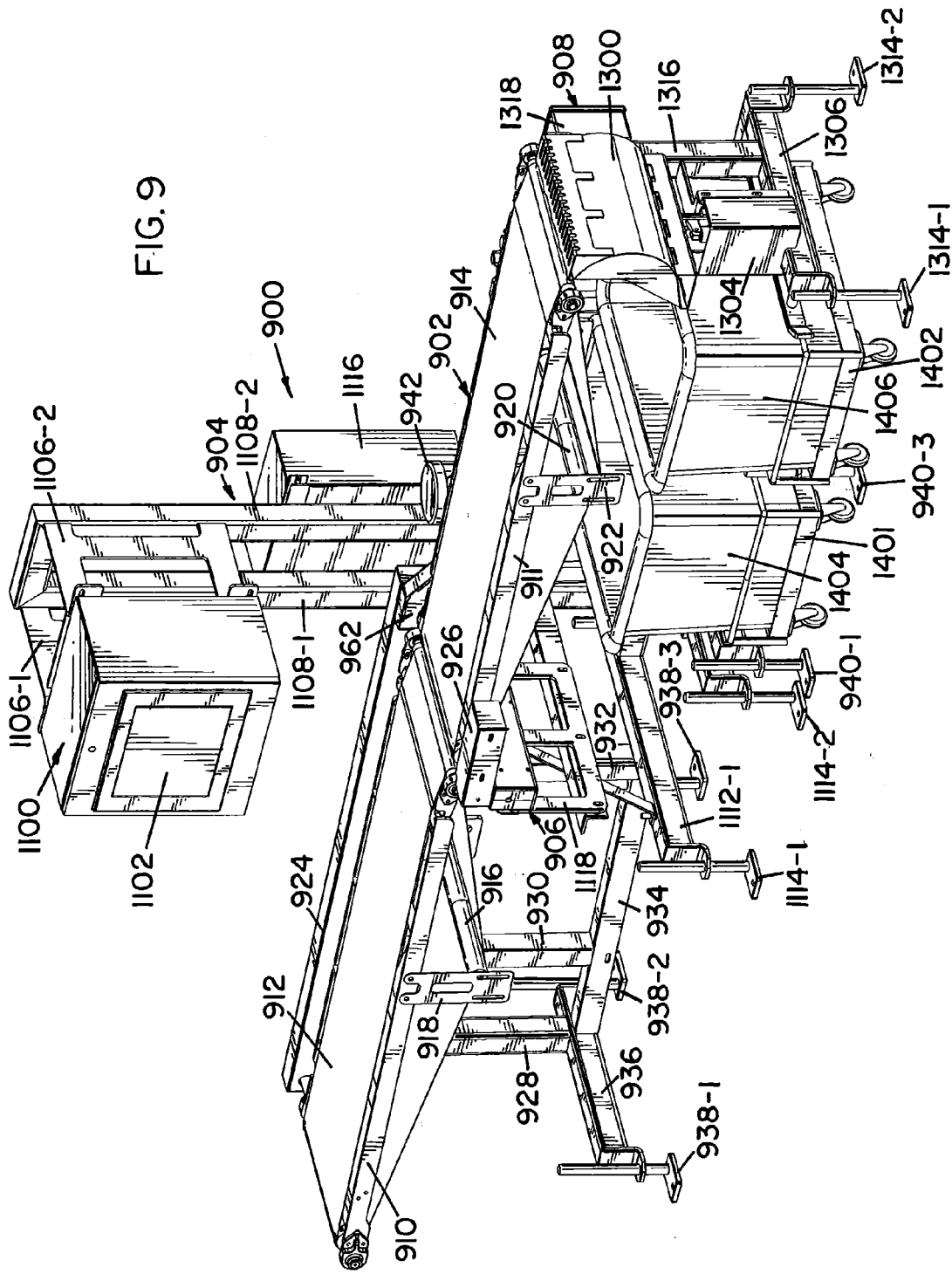
FIG. 9 is a front perspective view of another vision evaluation system of the present invention.

Referring to FIG. 9, a front perspective view of another embodiment of a vision evaluation system 900 is illustrated. This embodiment includes a conveyer assembly 902, an imaging assembly 904 and a rejection assembly 908. Conveyer assembly 902 and rejection assembly 908 are not connected to the imaging assembly 904 in this embodiment. This arrangement prevents vibrations created by the conveyer assembly 902 and the rejection assembly 908 from interfering with imaging taken place by the imaging assembly 904. FIG. 9 illustrates how the conveyer assembly 902, the imaging assembly 904 and the rejection assembly 908 come together to form the vision evaluation system 900.

Figure 10A:
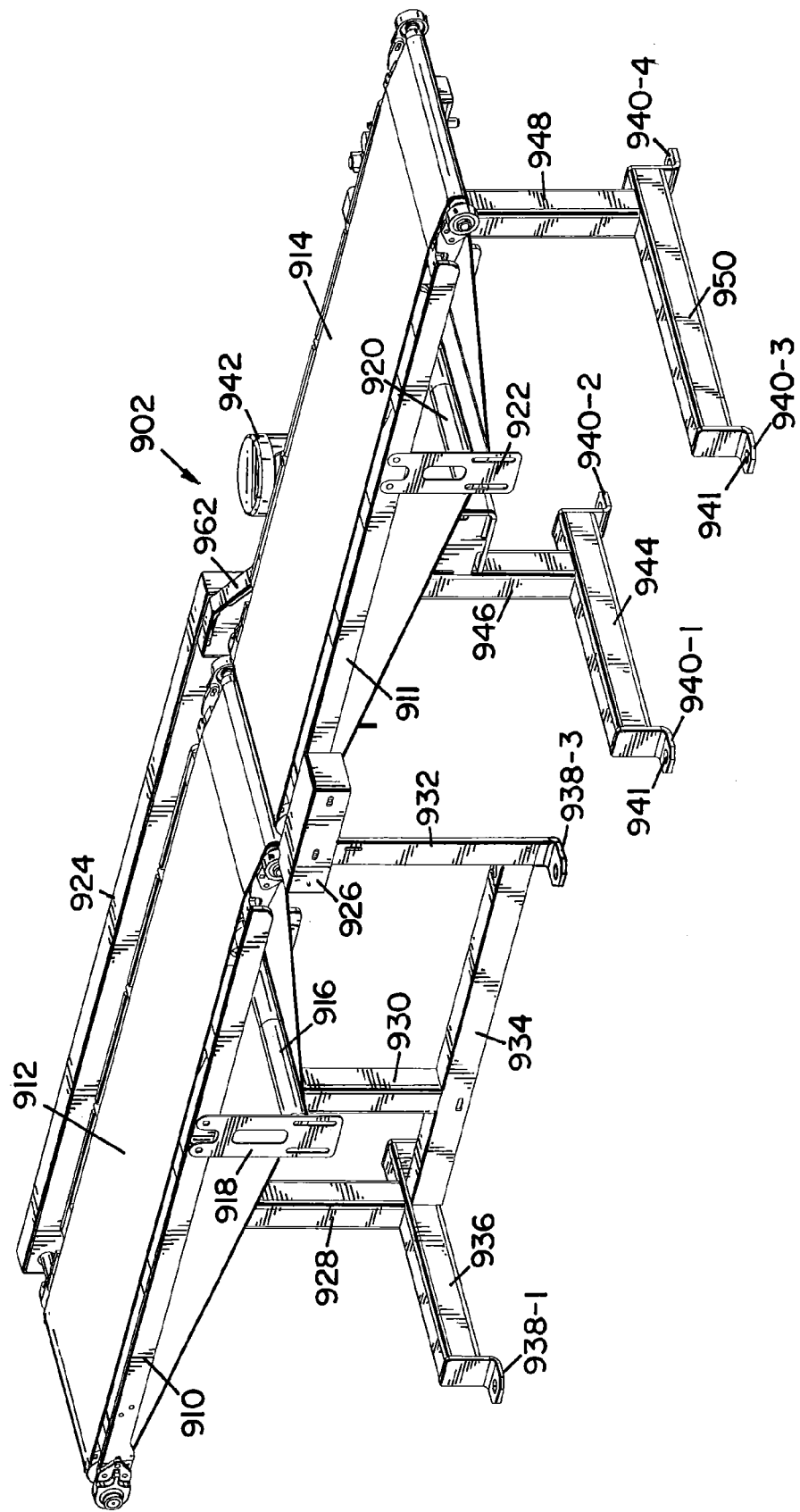
FIG. 10A is a front perspective view of a conveyer assembly of one embodiment of the present invention.
Figure 10B:
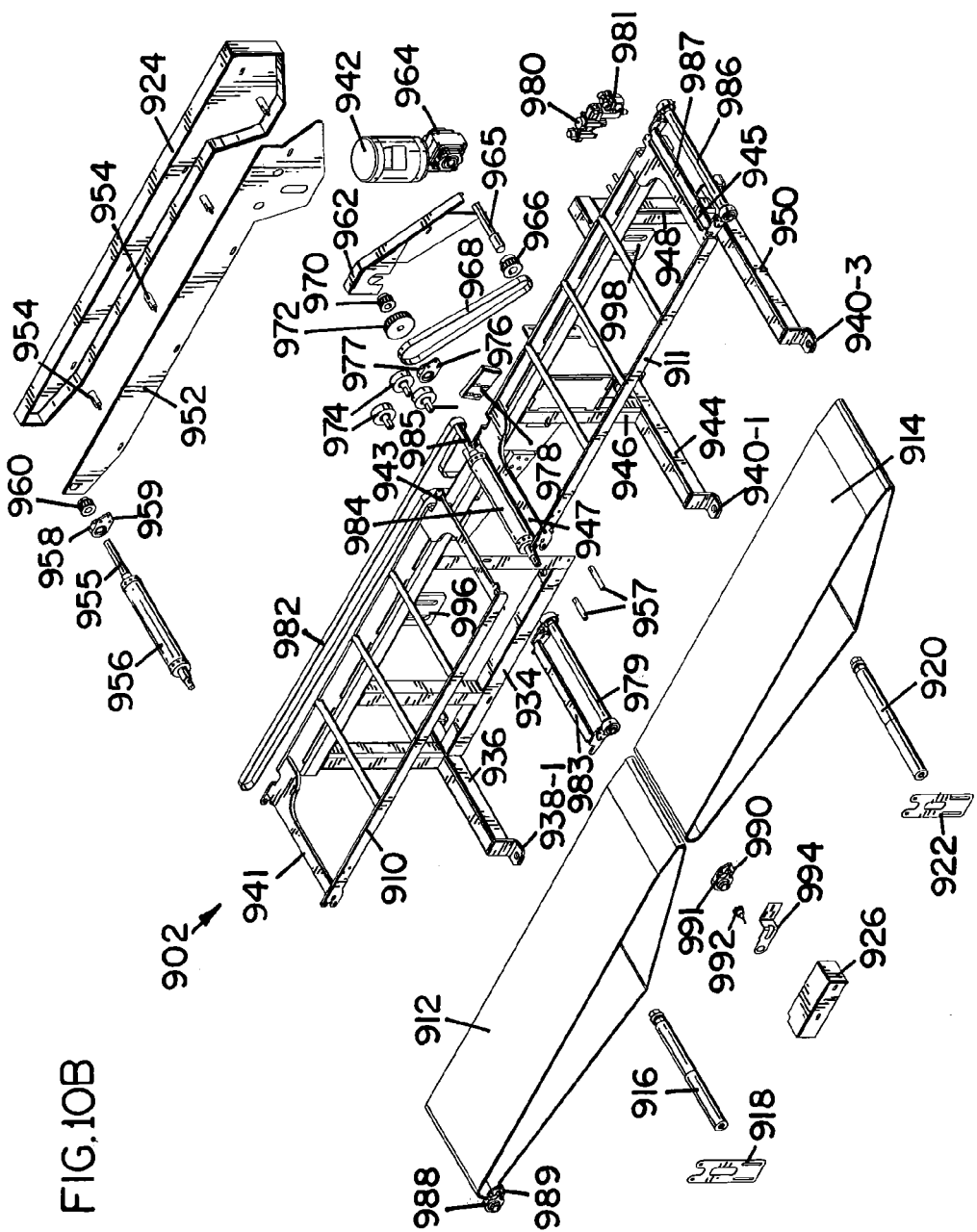
FIG. 10B is an unassembled front perspective view of the conveyer assembly of FIG. 10A.

FIGS. 10A and 10B illustrate the conveyer assembly 902 of FIG. 9. In particular, FIG. 10A illustrates a front perspective view of the conveyer assembly 902 and FIG. 10B illustrates an unassembled front perspective view of the conveyer assembly 902. Referring to FIGS. 10A and 10B a description of the components that make up the conveyer assembly 902 is provided. The conveyer assembly 902 includes two conveyer belt frames, conveyer belt frame 910 and conveyer belt frame 911. A base for conveyer belt frame 910 is made from conveyer frames 936 and 934. Conveyer frame 934 extends perpendicular from conveyer frame 936 as illustrated. Foot members 938-1, 938-2 (shown in FIGS. 9) and 938-3 support the conveyer frames 932 and 934 on a floor. Support members 928, 930 and 932 are coupled between conveyer frames 936 and 934 and conveyer belt frame 910 to position the conveyer belt frame 910 at a select height. Similarly, conveyer frames 944 and 950 form a base for conveyer belt frame 911. Foot members 940-1 and 940-2 coupled to conveyer frame 944, support conveyer frame 944 on the floor and foot members 940-3 and 940-4 coupled to conveyer frame 950, support conveyer frame 950 on the floor. Support member 946 is coupled between conveyer frame 944 and conveyer belt frame 911 and support member 948 is coupled between conveyer frame 950 and conveyer frame 911. The support members 946 and 948 position conveyer belt frame 911 at a select height that in this embodiment is the same height as conveyer belt frame 910. The foot members 938-1 through 938-3 and 940-1 through 940-4 each include an attaching aperture 941 that can be used to bolt the conveyer assembly 902 to the floor to reduce vibrations.

Coupled to conveyer belt frame 910 is roller assembly 956 coupled to a first end 941 of the conveyer belt frame 910 via bearing housing 988 and bearing housing 958. In particular, each bearing housing 988 and 958 includes a bearing (not shown) and a bearing bracket 989 and 959 respectively that is coupled to the first end 941 of the conveyer belt frame 910. On the other end, a second end 943, of the conveyer belt frame 910 a pivot assembly 981 is coupled. In particular, pivot assembly 979 includes bracket 983 that couples the pivot assembly 981 to the second end 943 of the conveyer belt frame 910. Coupled to frame 911 is roller assembly 984 coupled to a first end 947 of the conveyer belt frame 910 via bearing housing 976 and bearing housing 990. In particular, each bearing housing 976 and 990 includes a bearing (not shown) and a bearing bracket 977 and 991 respectively that is coupled to the first end 947 of the conveyer belt frame 911. On the other end, a second end 945, of the conveyer belt frame 911, a pivot assembly 986 is coupled. In particular, pivot assembly 986 includes bracket 987 that couples the pivot assembly 986 to the second end 945 of the conveyer belt frame 911. In the embodiment of FIG. 10B, a non-contact encoder 992 is coupled to the second conveyer frame 911 proximate the bearing 990 via bracket 994. The non-contact encoder 992 is used to determine the speed of the conveyer belt 914. A bearing guard 926 is further coupled to the second conveyer belt frame 911 to cover the non-contact encoder 992 and bearing 990 with the use of stand offs 957.

A first conveyer belt 912 is positioned over the first conveyer belt frame 910 and is engaged with the first roller assembly 956 and the first pivot assembly 981 that are rotationally mounted on opposite ends of the first conveyer belt frame 910. A first tension assembly bar 916 is rotationally coupled between a first and a second support plate 918 and 996. The first and second support plates 918 and 996 are coupled to opposite sides of the first conveyer belt frame 910. The first tension assembly bar 916 is further slidably coupled to the first and second support plates 918 and 996 to adjust the tension in the first conveyer belt 912. A second conveyer belt 914 is positioned over the second conveyer belt frame 911 and is engaged with the second roller assembly 984 and the second pivot assembly 986 that are rotationally mounted on opposite ends of the first conveyer belt frame 911. A second tension assembly bar 920 is rotationally coupled between a third and fourth support plate 922 and 998. The third and fourth support plates 922 and 998 are coupled to opposite sides of the second conveyer belt frame 911. The second tension assembly bar 920 is further slidably coupled to the third and fourth support plates 922 and 998 to adjust the tension in the second conveyer belt 914.

The conveyer belts 912 and 914 are rotated via conveyer motor 942. In particular, a reducer 964 is coupled to the motor 942 to provide a rotational output to drive shaft 965. Drive shaft 965 is coupled to a main pulley 966. The second roller assembly 984 includes a roller shaft 985. A first pulley 972 and a second pulley 970 are coupled to the roller shaft 985. A first drive belt 968 is engaged with the main pulley 966 and the first pulley 972 to rotationally move the roller shaft 985 of the second roller assembly 984. The second pulley 970 couple to roller shaft 985 is engaged with second belt 982. The second belt 982 is also engaged with a third pulley 960 that is coupled to a roller shaft 955 of the first roller assembly 956. Idlers, generally designated as 974 route the second belt between the second pulley 970 and the third pulley 960. A first and second belt guard covers 924 and 952 are used to cover the second belt 982 and the second and third pulleys 970 and 960. As illustrated, spacers, generally designated as 954 are used to space the first belt cover 924 from the second belt cover 952. A third belt cover 962 is further used to cover the first belt 968 and the first pulley 972.

Further illustrated in FIG. 10B are a pneumatic assembly 980 and an air solenoid 981. In one embodiment the pneumatic assembly 980 includes an air filter, regulator and a shut off. The filter is used for filtering the air and assists in removing at least some water form the air. The regulator of the pneumatic assembly 980 is used to regulate the air pressure to a rejection chute 1300 that is further described in detail below in regards to FIGS. 13A and 13B. The regulator is further used to regulate the air to an air knife assembly 1124 which is further described in detail below in regards to FIG. 12B. The shut off switch of the pneumatic assembly 980 is used to lock out air pressure to the vision evaluation system 900 when performing maintenance and cleaning. The air solenoid 981 is used to provide the air on and off to the air knife assembly 1124.

Figure 11A:
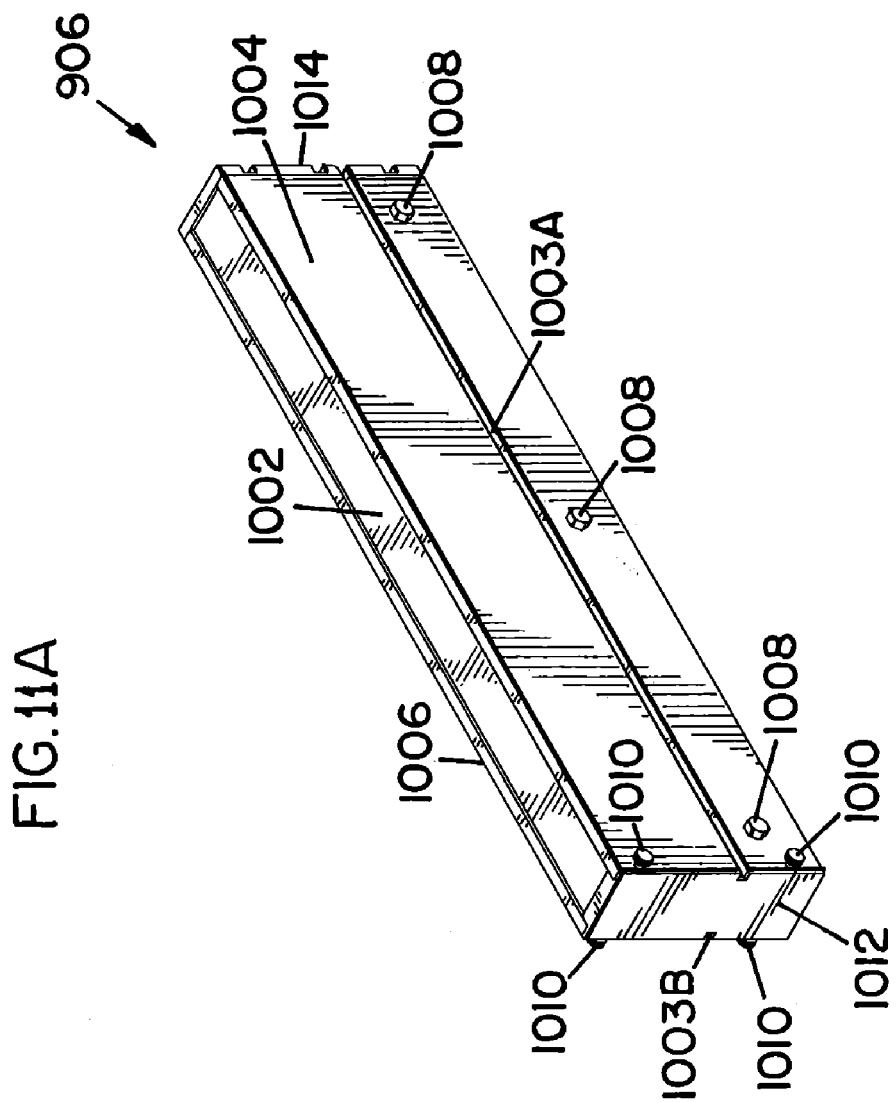
FIG. 11A is a side perspective view of a light box assembly of one embodiment of the present invention.

FIG. 11A illustrates one embodiment of a light box assembly 906. This embodiment includes a transparent protection plate 1002 that allows light to shine through, a first side plate 1004, a second side plate 1006, a first end cap 1012 and a second end cap 1014. The first and second side plates 1004 and 1006 are coupled together by fasteners 1008. In one embodiment, fasteners 1010 passing through the first and second side plates 1004 and 1006 near the first end cap 1012 selectively retain the first end cap 1012 to the first and second side plates 1004 and 1006. In one embodiment, fasteners 1010 are thumb screws that can be easily manipulated to remove the first end cap 1012. This allows for easy cleaning of the light box assembly 906. Moreover, in the embodiment of FIG. 11A, the first and second side plates 1004 and 1006 include exterior slots 1003A and 1003B respectfully. In one embodiment, slots 1003A and 1003B, provide a guide for retaining devices (not shown) that hold the light box assembly 906 in position in the vision evaluation system 900. They further allow an easily removable connection to the vision evaluation system 900 for the light box assembly 906 which further enables access to the light box assembly 906 for cleaning purposes.

Figure 11B:
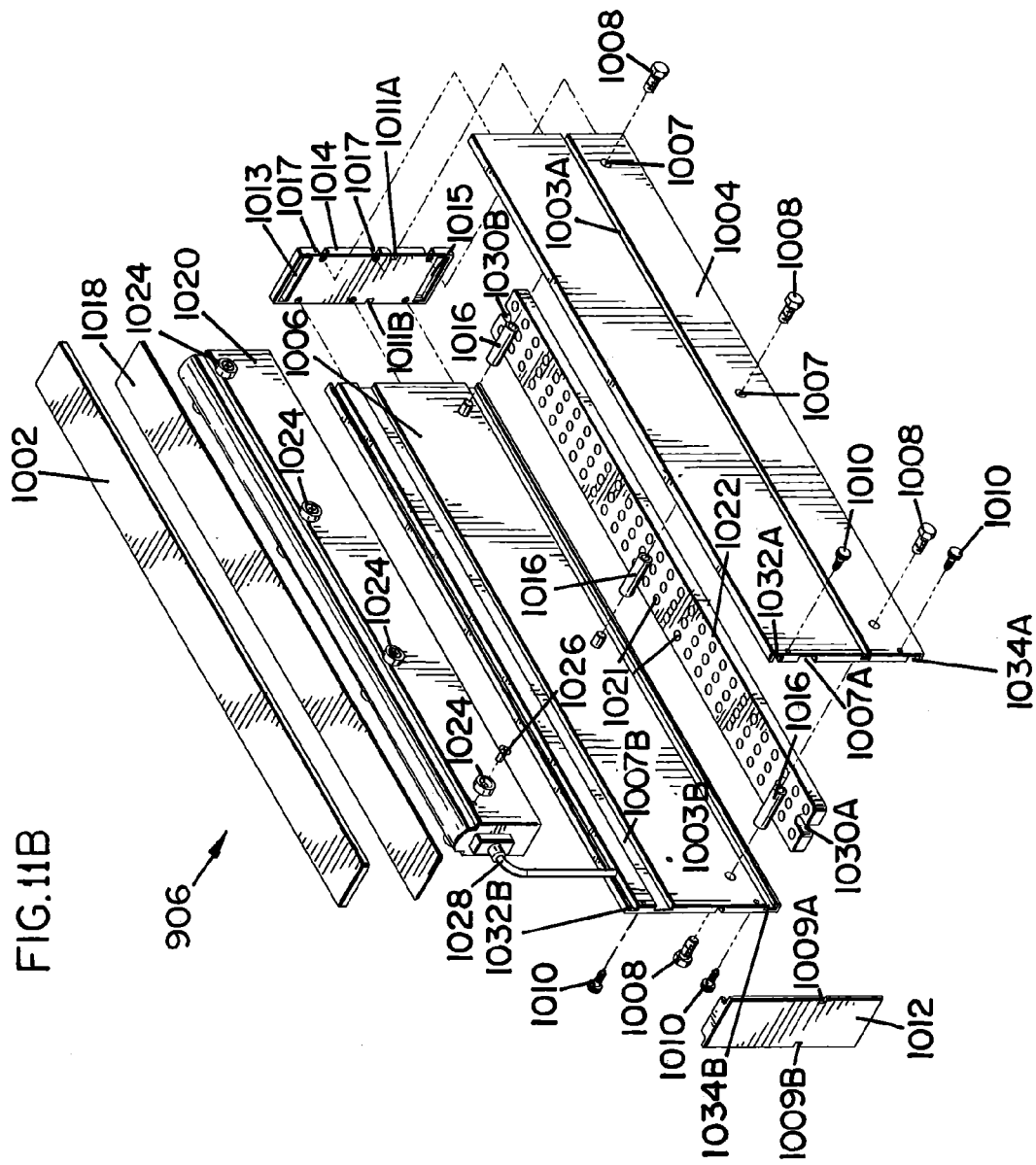
FIG. 11B is an unassembled side perspective view of the light box assembly of FIG. 11A.

FIG. 11B illustrates an unassembled light box assembly 906 of FIG. 11A. As FIG. 11B illustrates, the light box assembly 906 in this embodiment is made to easily be disassembled to allow for cleaning. As illustrated, the first side plate 1004 is coupled to the second side plate 1006 via fasteners 1008. Spacers 1006 are used to maintain the first side plate 1004 and the second side plate 1006 a select distance from each other. The light box assembly 906 includes a base plate 1022 that has a plurality of venting apertures 1021 that allow air to circulate in the light box assembly 906 to cool the light 1020. The base plate 1022 is received in interior slots 1034A and 1034B of the respective first and second side plates 1004 and 1006. An end of the base plate 1022 is further received in slot 1015 of the second end plate 1014. The base plate 1022 further includes cutout sections 1030A and 1030B that are located in the respective ends of the base plate 1022. The cutout sections 1030A and 1030B allow for a passage of a power cord 1028 to the light 1020. Having cutout sections 1030A and 1030B on either ends of the base plate 1022 allows for the base plate 1022 to be received in the slots 134A and 1034B in the first and second side plates 1004 and 1006 in different orientations. This allows the light box assembly 906 to be quickly assembled.

The light 1020 includes guides 1024 that are coupled along opposite sides of the light 1020. The guides 1024 of the light 1020 are received in interior slots 1007A and 1007B of the first and second side plates 1004 and 1006. The guides 1024 in the respective slots 1007A and 1007B retain the light 1020 in the light box assembly 1018. Further illustrated in FIG. 11B are polarized filter 1018 and the transparent protection plate 1002. Edges of the polarized filter 1018 and the transparent protection plate 1002 are received in interior slots 1032A and 1032B of the first and second side plates 1004 and 1006. Slots 1032A and 1032B retain the polarized filter 1018 and the transparent protection plate 1002 to align with the light 1020. Interior slot 1013 in the second end cap 1014 receives end portions of the polarized filter 1018 and the transparent protection plate 1002. The second end cap 1014 in this embodiment is fastened to the first and second side plates 1004 and 1006 via fasteners that pass through fastening apertures in the second end cap 1014. As discussed above, the first end cap 1012 is retained to the first and second side panels 1004 and 1006 via fasteners 1010 that can be easily removed. In cleaning the light box assembly 906 in this embodiment, the first end cap 1012 is removed and the polarized filter 1018 and the transparent protection plate 1002 are slid out of interior slots 1032A and 1032B. Then the light guides 1024 are slid out of interior slots 1007A and 1007B and base plate 1022 is slide out of slots 1034A and 1034B. Once the elements are cleaned they are reassembled in reverse order. As also illustrated in FIG. 11B is the first end cap 1012 including exterior slots 1009A and 1009B that align with exterior slots 1003A and 1003B in the respective first and second side plates 1004 and 1006. Likewise, the second end cap 1014 includes exterior slots 1011A and 1011B that align with exterior slots 1003A and 1003B of the first and second side plates 1004 and 1006. As discussed above the exterior slots 1003A, 1003B, 1009A, 1009B, 1011A and 1011B are used in one embodiment to selectively position the light box assembly 906 in the imaging assembly 904.

Figure 12A:
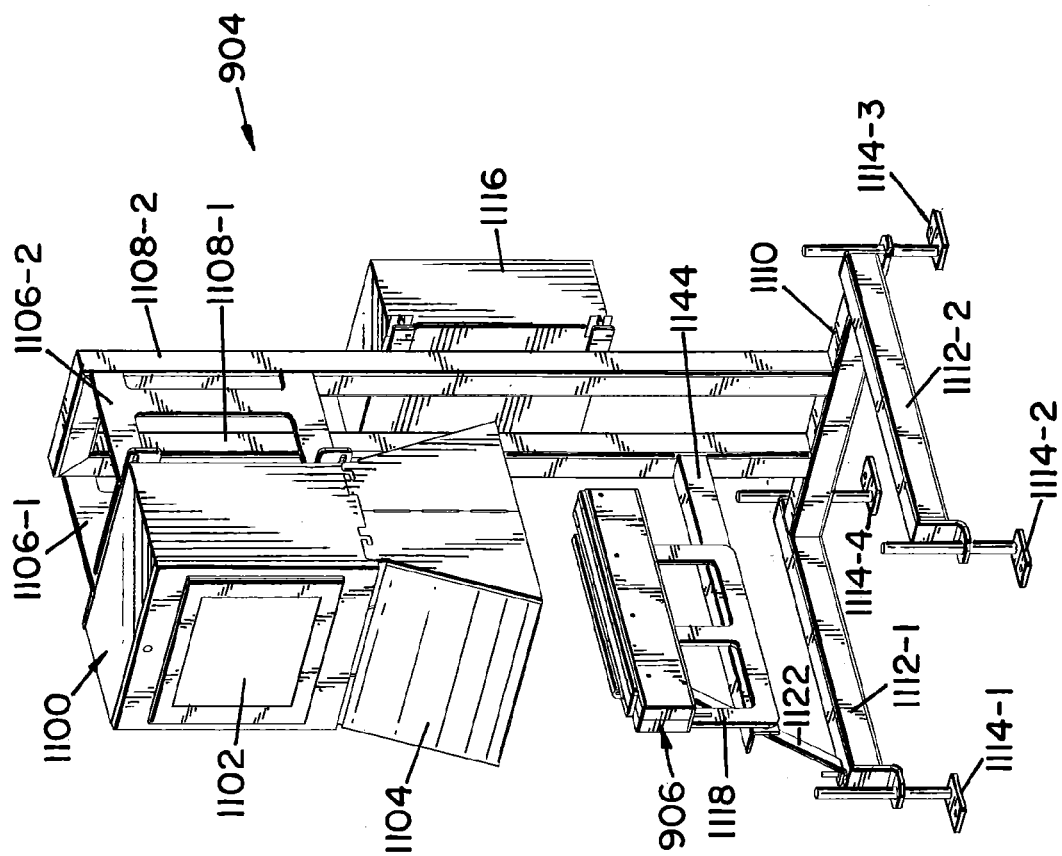
FIG. 12A is a side perspective view of an imaging assembly of one embodiment of the present invention.

Referring to FIGS. 12A and 12B an embodiment of an imaging assembly 904 is illustrated. In particular, FIG. 12A illustrates an assembled side perspective view of the imaging assembly 904 and FIG. 12B illustrates an unassembled side perspective view of the imaging assembly 904. The imaging assembly 904 includes image frame members 1110, 1112-1 and 1112-2 formed in generally a U-shape. Image foot members 1114-1 through 1114-4 extend from respective image frame members 1110, 1112-1 and 1112-2. Each foot member 1114-1 through 1114-4 engages a surface upon which the image assembly 904 rests. Image supports 1108-1 and 1108-2 extend up generally perpendicular from image frame member 1110 as illustrated. A support arm 1144 extends generally perpendicular from the first image support 1108-1 a select distance from image support 1110. A light support bracket 1118 is coupled to the support arm 1144. In one embodiment, spacers 1142 provide a space between the light support bracket 1118 and the support arm 1144. The light support bracket 1118 in this embodiment is coupled to the light box assembly 906. Also coupled to the light support plate 1118 is an air knife assembly that includes an air knife bracket 1124 and an air knife 1126. The air knife 1126 blows air across a top surface (e.g. a surface of the transparent protection plate 1002) of the light box assembly 906 when needed to assist in removing any dust or other particle build-up on the surface of the light box assembly 906. In one embodiment the activation of the air knife 1126 is based on a timer. Further in one embodiment, a support bar 1122 extending between image frame member 1112-1 and the light support bracket 1118 provides further support for air knife 1126 and the light box assembly 906. Spacer 1140, spaces an upper end of the support bracket 1122 at distance from the light support bracket 1118.

Proximate a mid portion of the first and second imaging supports 1108-1 and 1108-2 a control panel 1116 is attached. The control panel 1116 is attached on the imaging supports 1108-1 and 1108-2 on an opposite side than the support arm 1144 extends. The control panel 1116 houses controls for the vision evaluation system 900. The control panel 1116 is attached to the imaging supports 1108-1 and 1108-2 via fasteners 1138 extending from support attaching tabs 1136 on the respective imaging supports 1108-1 and 1108-2. The fasteners 1138 are received in notches in panel attaching tabs 1134-1 through 1134-4 on the control panel 1116. A camera housing bracket is attached to the first and second image supports 1108-1 and 1108-2 proximate an end of the first and second image supports 1108-1 and 1108-2 that is opposite an end coupled to image frame member 1110. The camera housing bracket includes a first attaching bracket 1106-1 extending from the first image support 1108-1 in the same direction as the support arm 1144 extends from the first image support 1108-1. The camera bracket also has a second attaching bracket 1106-2 that extends from the second image support 1108-2 in the same direction as the first attaching bracket 1106-1. Braces 1105-1 and 1105-2 are coupled between the first and second attaching bracket 1106-1 and 1106-2.

A camera housing 1100 is coupled to the first and an second attaching brackets 1106-1 and 1106-2 using fasteners (not shown) passing through slots 1130 in the respective first and second attaching brackets 1106-1 and 1106-2 and engaging the camera housing 1100. In one embodiment, spacers 1132 are used to space the camera housing 1100 from the first and second attaching brackets 1106-1 and 1106-2. The camera housing 1100 includes a display 1102. In one embodiment, the display is a touch screen display 1102 that not only displays information but allows operators to input information into the vision evaluation system 900. As further illustrated in FIGS. 12A and 12B, a shield 1104 is used in one embodiment. The shield 1104 is coupled to an underside of the camera housing 1100. The shield 1104 is used to prevent light from light sources other than light source 906 from entering camera lenses in the camera housing 1100.

Figure 12C:
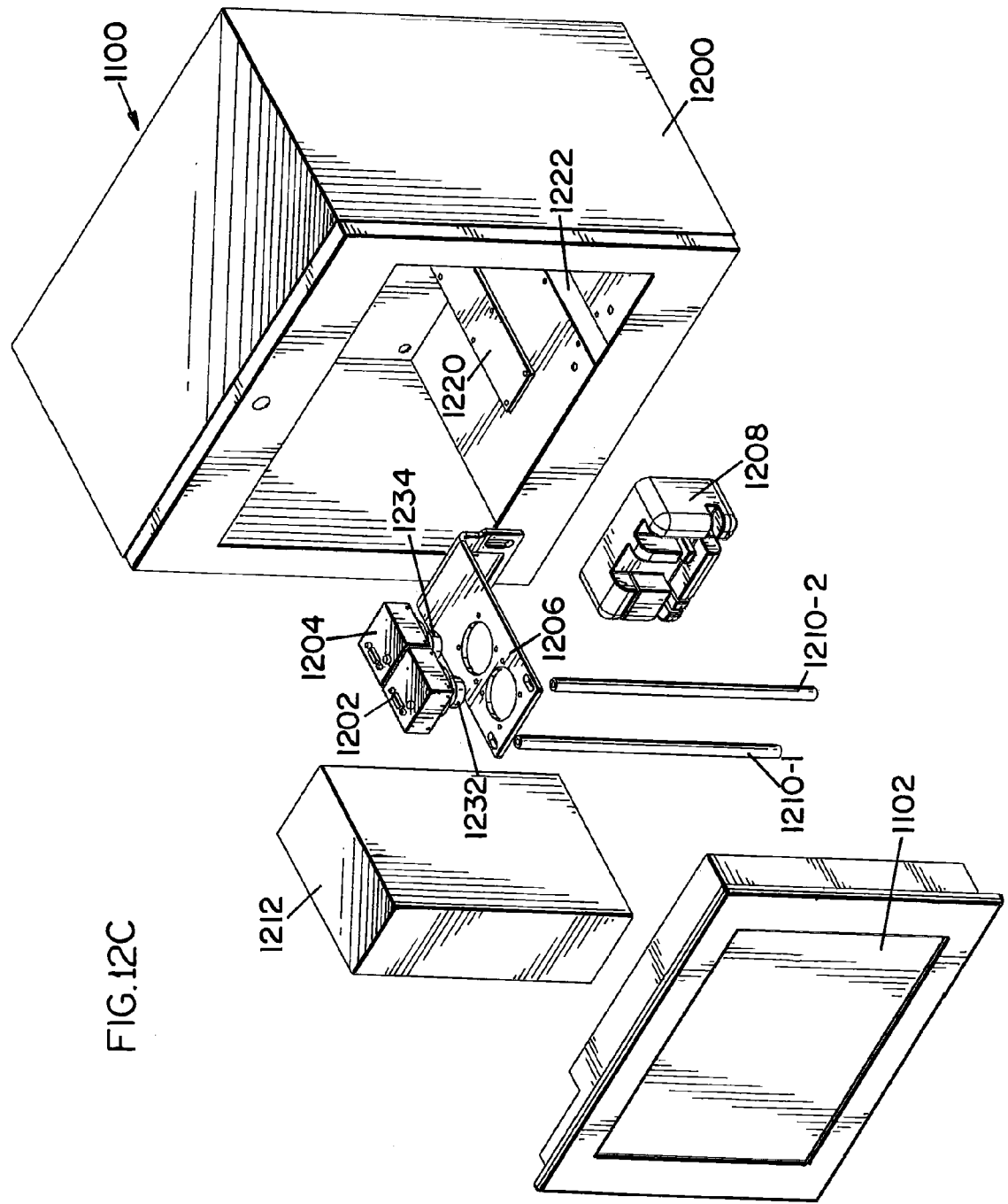
FIG. 12C is a side perspective view of an unassembled camera housing of one embodiment of the present invention.

An illustration of an unassembled camera housing 1100 of one embodiment is shown in FIG. 12C. The camera housing 1100 includes an opening 1222. A housing transparent plate 1220 is coupled over the opening 1222 inside the camera housing 1100. A camera mounting bracket 1206 is coupled inside the camera housing 1100. In one embodiment, first and second camera supports 1210-1 and 1210-2 are further used to support the camera mounting bracket 1206 in the camera housing 1100. A first camera 1202 and a second camera 1204 are mounted to the camera mounting bracket 1206. The first and second cameras 1202 and 1204 are position so their lenses face the opening 1222 in the camera housing 1100. The first and second camera 1202 and 1204 both include polarized filters 1232 and 1234 respectively in front of their lenses. The polarized lens 1232 of the first camera 1202 is polarized at 90° in relation to the polarized film 1018 over the light 1006 of the light box 906. The polarized lens 1234 on the second camera 1204 is polarized at 0° in relation to the polarized film 1018 over the light 1006 of the light box 906. The use of polarized lens 1234 on the second camera enables images taken from the first and second cameras 1202 and 1204 to have the same scale aspect. A control system 1212 in this embodiment is received in the camera housing 1100. The control system 1212 includes one or more processors, memory and software modules used to control functions of the vision evaluation system 900. The control system 1212 is further discussed below. Further illustrated in FIG. 12C, is an interface board 1208 that is located in this embodiment inside the camera housing 1100. The interface board 1208 is used to provide connections and communications between elements of the vision evaluation system 900 such as the control system, the cameras 1202 and 1204, the rejection assembly 908 and the display 1102.

Figure 13A:
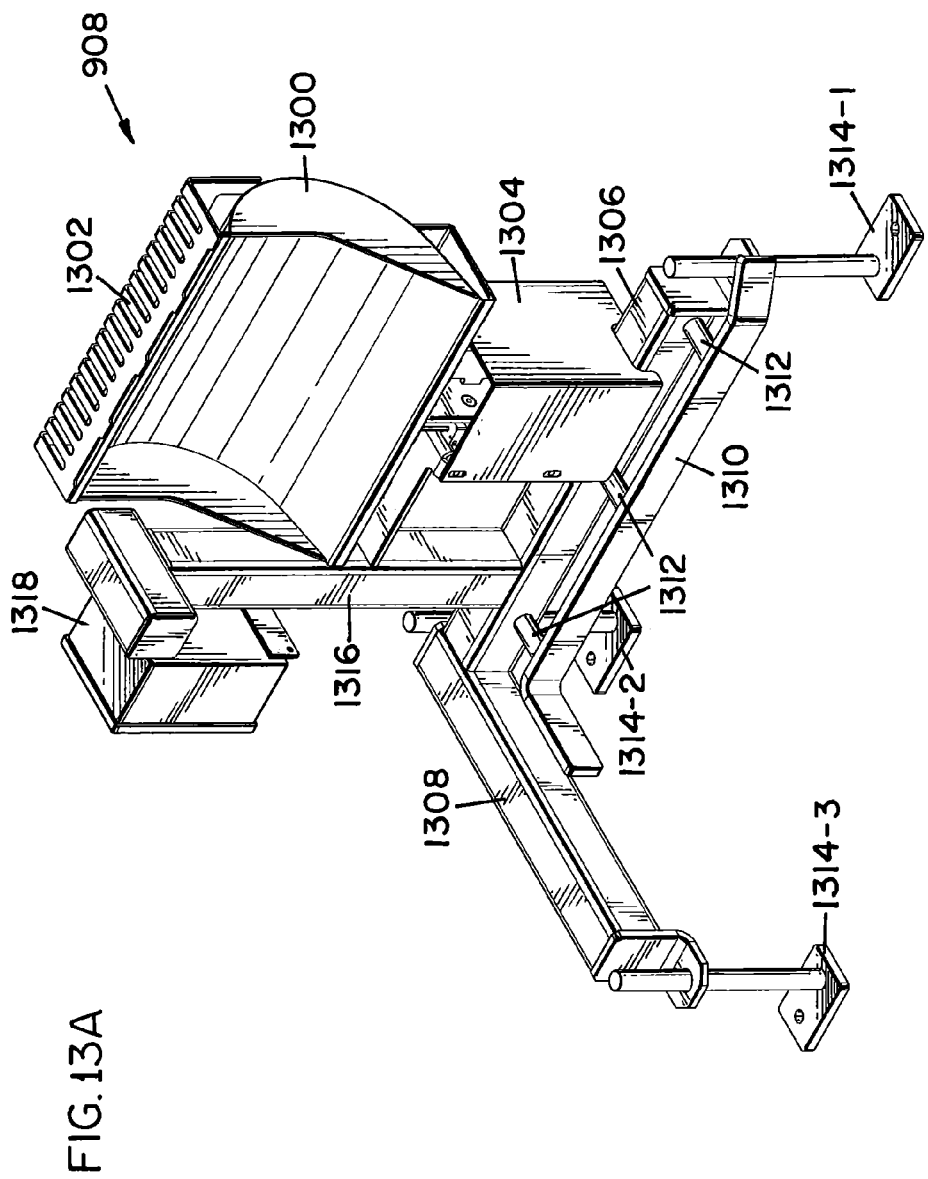
FIG. 13A is a side perspective view of a rejection assembly of one embodiment of the present invention.
Figure 13B:
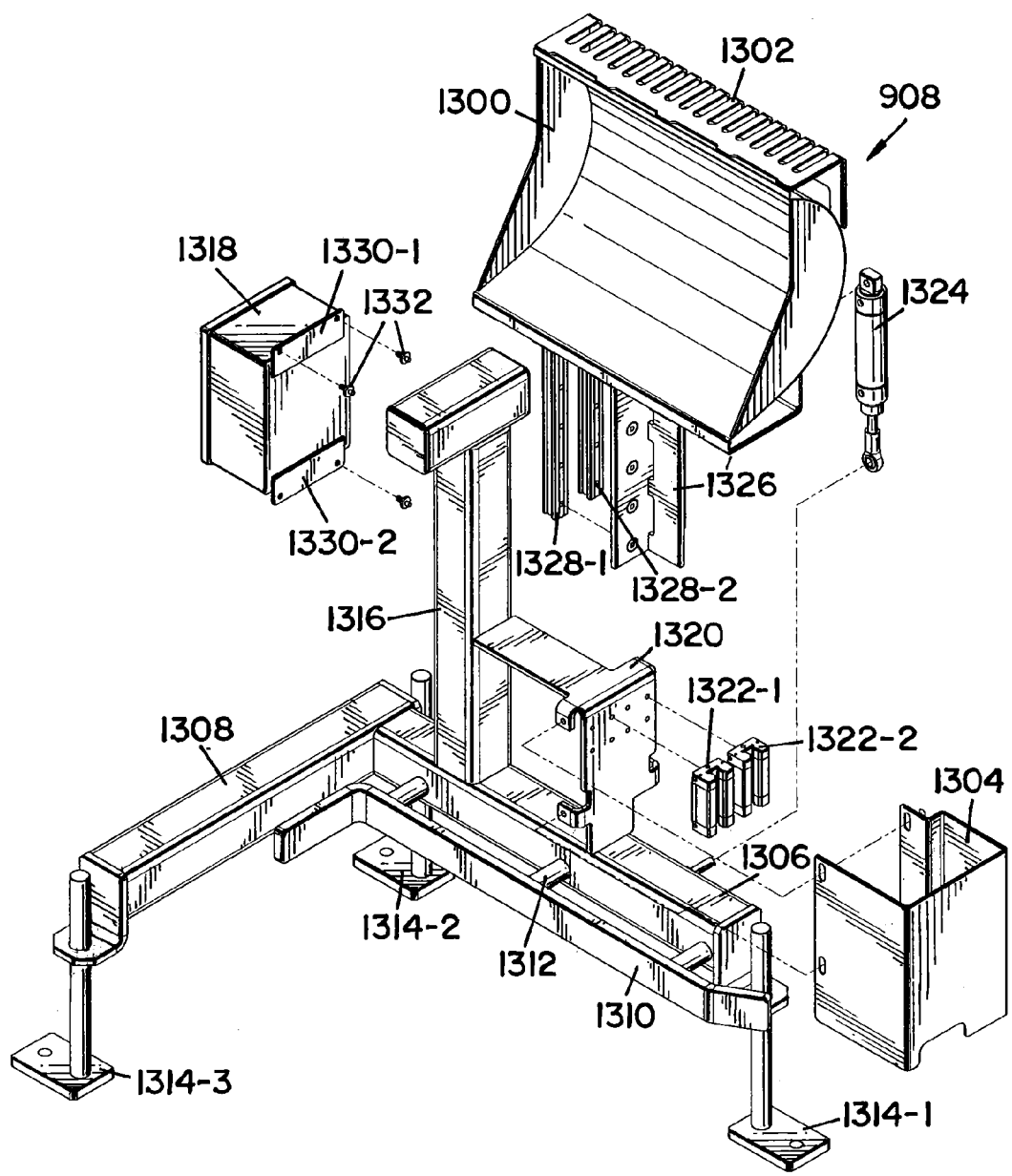
FIG. 13B is an unassembled side perspective view of the rejection assembly of FIG. 13A.

Referring to FIGS. 13A and 13B an illustration of the rejection assembly 908 of one embodiment is illustrated. In particular, FIG. 13A illustrates a side perspective view of an assembled rejection assembly 908 and FIG. 13B illustrates a side perspective view of an unassembled rejection assembly 908. The rejection assembly 908 includes first and second rejection frame members 1306 and 1308 that are coupled together in generally an L-shape. Rejection foot members 1314-1 through 1314-3 are coupled to the first and second rejection frame members 1306 and 1308 at select locations to provide support of the frame members 1306 and 1308 on a surface the rejection assembly 908 is resting. In one embodiment, a bumper rail 1310 is attached to the first rejection frame member 1306. The bumper rail 1310 among other things, provides guidance for a mobile base 1402 of a rejection container 1406 to position the rejection container 1406 to receive rejected product (illustrated in FIG. 9).

A rejection support member 1316 extends up perpendicular from the first rejection frame member 1306 proximate the second rejection frame member 1308. A generally L-shaped mounting plate 1320 is coupled between the rejection support member 1316 and the first rejection frame member 1306. First and second receiving rail blocks 1322-1 and 1322-2 are coupled to a surface of the mounting plate 1320 that is generally extends perpendicular to the first rejection frame member 1306. The rejection assembly 908 also includes a chute 1300 to redirect products not passing an inspection of the vision evaluation system 900. The chute 1300 includes a product guide 1302 that guides products that pass the inspection beyond the chute 1300. The product guide 1302 is coupled proximate a top end of the chute 1300. A first rail 1328-1 and a second rail 1328-2 extend proximate from a bottom end of chute 1300. The first rail 1328-1 slidably engages the first receiving rail block 1322-1 and the second rail 1328-2 slidably engages the second receiving rail block 1322-2. Further extending from the bottom end of the chute 1300 is a rail cover 1326. A pneumatic cylinder 1324 is coupled between the rail cover 1326 and the first rejection frame member 1306. The pneumatic cylinder 1324 raises and lowers the chute 1300 depending on whether the then current product passing the chute 1300 passes or fails an inspection. Further a rejection control housing 1318 is coupled to the rejection support member 1316. In particular, retaining plates 1330-1 and 1330-2 of the rejection control housing 1318 are couple to the rejection support member 1316 via fasteners 1332. The rejection control housing 1318 includes controls for the pneumatic cylinder 1324. In one embodiment, the controls include a solenoid valve that switches on an off air from the pneumatic assembly 980 to the pneumatic cylinder 1324. A chute activation mechanism cover 1304 covers the pneumatic cylinder 1324 and the rail cover 1326. The chute activation mechanism cover 1304 is coupled to the mounting plate 1320.

Figure 14:
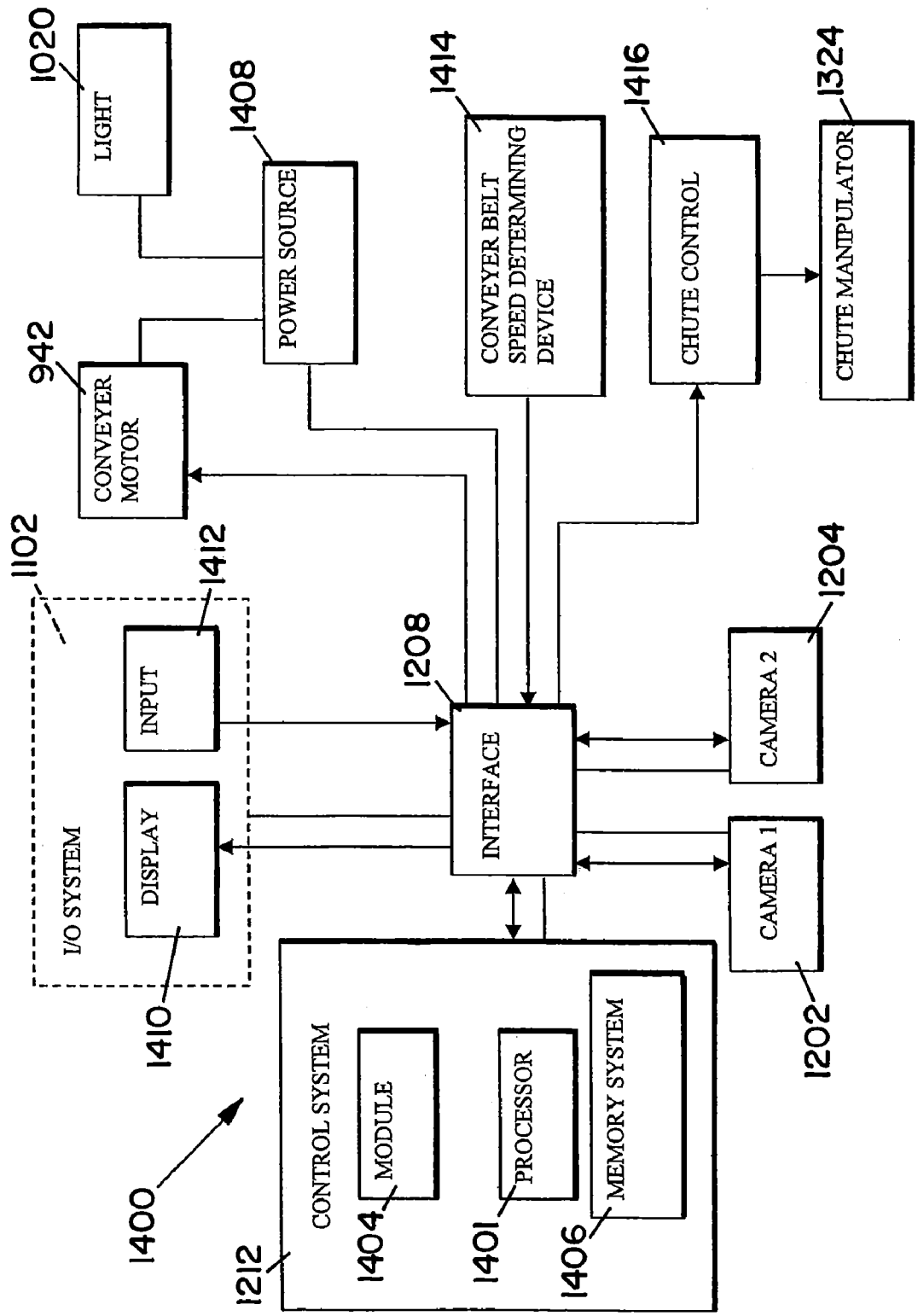
FIG. 14 illustrates a block diagram of an embodiment of vision evaluation system of the present invention.

Referring to FIG. 14, a block diagram of one embodiment of a vision evaluation system 1400 of one embodiment of the present invention is illustrated. This embodiment includes a control system 1212 that controls aspects of the vision evaluation system 1400. The control system 1212 (which can be referred to as a controller) in this embodiment includes a processor 1401 to process information, a memory system 1406 to store information and a software module 1404 to provide instructions to the processor 1401. Generally embodiments of control system 1212 may be implemented in digital electronic circuitry, or with a programmable processor 1401 (for example, a special-purpose processor or a general-purpose process such as a computer) firmware, software (1404), or in combinations of them. Apparatus embodying these techniques may include appropriate input and output devices 1102, a programmable processor 1401, and a storage medium 1406 tangibly embodying program instructions for execution by the programmable processor 1401. A process embodying these techniques may be performed by a programmable processor executing a program of instructions to perform desired functions by operating on input data and generating appropriate output. The techniques may advantageously be implemented in one or more programs that are executable on a programmable system including at least one programmable processor coupled to receive data and instructions from, and to transmit data and instructions to, a data storage system 1401, at least one input device 1412, and at least one output device 1410. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing may be supplemented by, or incorporated in, specially-designed application-specific integrated circuits (ASICs).

The control system 1212 of this embodiment is coupled to an interface 1208. The interface in this embodiment generally provides an interface for at least some power and communication functions. For example, in this embodiment, interface of the power source 1408 is provided to the control system 1212, an input/output system 1102, the first camera 1202 and the second camera 1204. The interface 1208 provides select power outputs required by the devices. The interface 1208 uses common techniques and components known in the art to achieve select power requirements of the devices. The power source 1408, in this example, also provides power to the light source 1020 and the conveyer motor 942. The interface, as discussed above, also provides a communication interface between devices of the vision evaluation system 1400. For example, interface 1208 provides an interface between an input 1412 of the input/output system 1102. The input 1412 provides a user a way to input information to the control system 1212, such as but not limited to, instructions regarding adjustments to the vision evaluation system 1400 and software used to run the processor 1401 of the control system 1212. The input 1412 may be any type of input device, such as but not limited to, a touch screen, a keyboard and an input port. The output device (of the input/output system 1102) which in this example is a display 1410 is also in communication with the interface 1208 to receive information from the processor. Such information may include, but is not limited to, the status of evaluated packages and the current settings of the vision evaluation system 1400.

As FIG. 14 further illustrates, the first camera 1202 and the second camera 1204 are also in communication with the control system 1212 via the interface 1208. In embodiments, the control system 1212 directs the cameras 1202 and 1204 to takes pictures simultaneously. In particular, in this embodiment, cameras 1202 and 1204 are line scan cameras that capture line scan image data at a select frequency. Hence, in this embodiment, while the vision evaluation system 1400 is in operation, the cameras are continuously taking images at a select frequency and storing line scan image data in buffers of the memory system 1406. The control system 1212 evaluates the stored line scan images to determine if a package has been capture. Only once it has determined that a package has been captured does it start its analyzing functions. An evaluation of the polarized package image from the line scan image data from the first camera 1202 is done to then determine the orientation of the package and the location of the seal of the package. Once that is complete, an analysis of the package image from the line scan image data from the second camera 1204 takes place to determine the quality of the seal. An example of the location of a seal of the first package image from the first camera and the analysis of the corresponding seal in the second package image from the second camera is illustrated in the flow diagram 600 of FIG. 6 described above. Besides, evaluating the seal, in other embodiments other evaluations of the package can take place. For example, in one embodiment, once the coordinate system is established on the second image, the second image is evaluated to determine if a pad used to absorb fluids is within the package. In yet another embodiment, the second image is further evaluated to determine if the product is within the package. In these embodiments, it is determined based on the coordinate system where the pad or the product is likely to be located. The pixels at those determined locations are then analyzed to determine if they are present. For example, regarding determining if the pad is present, it is likely that if the pad is present it will be within a select central area to the package. Hence, the pixels of the select central area, based on the determined coordinate system, are evaluated. If light passes through the package, the pixels would indicate nothing is present at that select central area and that it is likely the pad is missing. However, the pixels indicate no light passed through it is likely the pad is present. A similar analysis is done in a select area of a package that is likely to contain the product.

The block diagram of FIG. 14 further illustrates the use of a conveyer belt speed determining device 1414 that is in communication with the control system 1212 via interface

1208. The conveyer belt speed determining device 1414 provides conveyer speed information regarding the first and second conveyer belts 912 and 914 to the control system 1212. The control system uses the speed information in coordinating functions of the vision evaluation system 1400. Different types of conveyer belt speed determining systems 1414 can be used. For example, an encoder 992 illustrated in FIG. 10B could be used as the conveyer belt speed determining device 1414. In another embodiment, the conveyer belt speed determining device 1414 is a direct measurement device. As discussed above, the control system 1212 uses the speed information of the conveyer to determine the rate (frequency) of taking the images as well as determining the speed needed to process the image data. Further, information regarding the speed of the conveyer belts 912 and 914 is further needed to determine when to activate the chute control 1416 that controls the chute manipulator 1324 when it has been determined that a bad package has been detected. In one embodiment, the control system 1212 is coupled to control the conveyer motor 924 to select the speed of the conveyer belts 912 and 914. Further in one embodiment, the time that the chute manipulator 1324 is activated is not based on a set period (since two bad packages could be located sequentially on the convey belts 912 and 914 and un-necessary wear on the parts of the chute assembly 908 opening and closing can be avoided). In this embodiment, the control system 1212 determines how long to activate the cute manipulator 1324 via the chute control 1416.

Since the lenses of the cameras 1202 and 1204 cannot occupy the same space, the perspective of the images taken by the camera 1202 and 1204 will be off a little. In operation of embodiments, images from the cameras 1202 and 1204 are first calibrated to account for the differing perspective of the cameras 1202 and 1204. Calibration allows for an accurate coordinate system between the two images. FIG. 15A, illustrates a calibration flow diagram 1500 of one embodiment. As illustrated, this process starts by placing an image having reference points to be captured by the cameras 1202 and 1204 (1502). The calibration image 1520 used in one embodiment is a column of parallel lines 1522 as illustrated in FIG. 15B. Both cameras take a picture of the calibration image (1504). Differences between reference points in the two images are then determined (1506). In the embodiment of the calibration image of FIG. 15B, each reference point is a mid point location 1524 on each line 1522 on the image 1520. As FIG. 15A illustrates, once the differences are determined, the differences are then used to set up an interpolation algorithm to adjust image data from one of the cameras 1202 or 1204 in relation to the image data from the other camera 1202 or 1204 (1508). Hence, in one embodiment, only one set of image data is interpolated to correspond to the other image data.

Referring to FIG. 16 an application flow diagram 1600 of one embodiment is illustrated. As flow diagram 1600 illustrates, this process starts by first determining the speed of the conveyer belts 912 and 914 (1602). The control system 1212 then calculates the frequency of capturing simultaneous images by the cameras 1202 and 1204 (1604). Based on the calculated frequency, each camera 1202 and 1204 captures simultaneous line scan images (1606). Each set of line scan image data are stored in a memory 1406 (1608). In one embodiment, buffers are used to store the line scan image data. Each row of stored line scan image data is then evaluated (1610). In one embodiment, the rows of line scan image associated with the first camera 1202 with the polarized filter at 90 degrees (polarized line scan image) from the light are evaluated. In embodiments, the corresponding rows of line scan image data from the second camera 1204 are tracked in buffers so the association with the rows of line scan image from the first camera is maintained. It is then determined if pixel data in the row of line scan image indicate the start of a package to be evaluated (1612). If the pixel data in a row of the line can image does not indicate the beginning of a package at (1612), a next row in the memory of the line scan image is evaluated at (1610). If the pixel data in a row of the line scan image indicate the beginning of a package at (1612), the rows of line scans are gathered (1614). It is then determined if the pixel data in the line scan image indicated an end of the package has been detected (1616). This would occur when all the pixel data in a line scan image indicate nothing has blocked the light. If it is determined that the end of the package has not been detected at (1616), the rows of pixel data are continued to be gathered at (1614). If, however, an end of the package has been detected at 1616, evaluation of a first polarized image made up of the rows of pixels begins at (1618).

In evaluating the first polarized image, the processor 1401 of the control system 1212 selects reference point in the rows of pixels is determined (1618). An X-Y coordinated system based on the reference point is then created (1620). Next an angle of rotation of the X-Y coordinate system in relation to the reference point is determined (1622). This takes into account that when a package is set on the conveyer its orientation can be in any direction and that orientation has to be known to fit the X-Y coordinate system properly over the image. Once, the X-Y coordinate system has been established, select areas that need to be analyzed are mapped out (1624). The areas to be mapped out can be the seal areas as discussed above, a pad area and a product area. Further as discussed above, the polarized image provides a better indication of specific areas, such as the seal areas, that aid in setting out the X-Y coordinates and the mapping of the select areas. The purpose of mapping out the specific areas is to reduce the computing resources that would be required if all the areas of an image had to be analyzed. Once, the mapped out areas to be analyzed has been determined, the corresponding rows of line scan image data that make the second related image are gathered (1626). The X-Y coordinate system is then applied to the second image (1628). The determined mapped out area set out in the X-Y coordinate system are then evaluated on the second image (1630). One type of evaluation is based on a pixel analysis as discussed above. In embodiments, implementing the pixel analysis, parameters used by the processor 1401 of the control system 1212 can be adjusted to achieve a desired outcome. If the package passes (1632), the process continues at (1610) where each row of line scan images are evaluated to find the beginning of the next package. If the package does not pass the analysis at (1632), the rejection chute is activated (1634) to remove the package from processing. The process then continues at (1610) where each row of line scan images are evaluated to find the beginning of the next package.

Figure 17A:
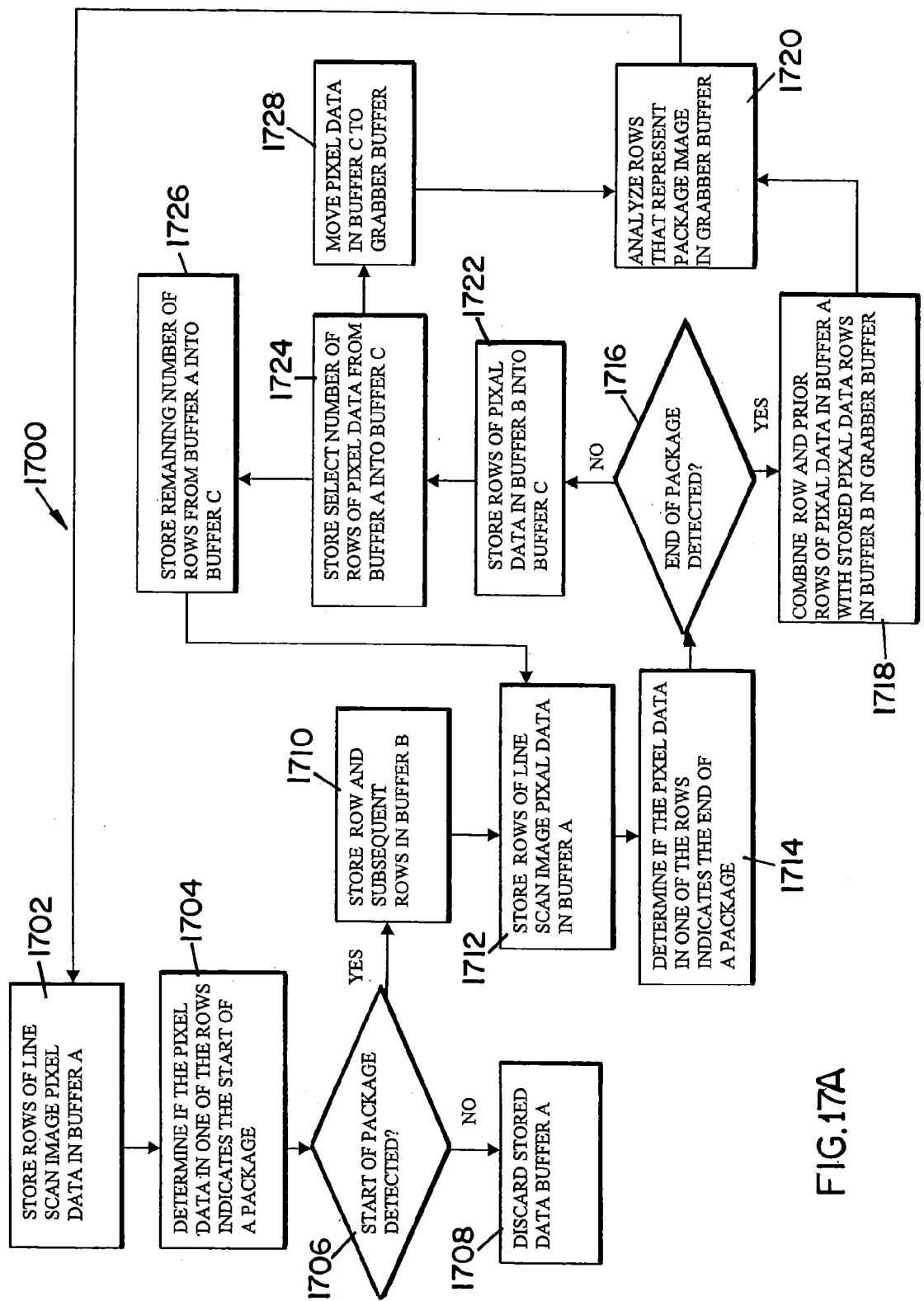
FIG. 17A illustrates a buffer flow diagram of one embodiment of the present invention.

In some embodiments, the gathering of rows of line scan image data (pixel data) that represent pixels of part of a package image as generally illustrated in steps (1608) through (1616) set out above is done by placing the rows of line scan image data in temporary buffers. Once the whole image of the package (rows of pixel data that include parts of the package) is saved in a buffer, the analysis begins. An example of one embodiment using the temporary buffers is illustrated in buffer flow diagram 1700 of FIG. 17A and buffer illustration 1750 of FIG. 17B. In this example, buffer A is initially filled row by row with in coming line scan image data from one of the cameras 1202 or 1204 (1702). The size of buffer 1702 in this example is 1024 by 400 bits. That is, buffer A has memory locations for 400 rows of 1024 bits of pixel data. The size of the buffer is dependant on the number of pixels in the camera line scan image (i.e. 1024 pixel data in this example which would cover the width of the conveyer) and the number of rows desired. The number of rows desired is dependant on the size of the packages being analyzed. Once, buffer A is filled, each row is analyzed to determine if any of the pixel data in the row indicates the detection of a beginning of a package (1704). If no beginning is detected at (1706), the stored rows of line scan image data in buffer A are discarded or wrote over (1708). If the beginning of the package is detected in a row of line scan image data, that row and subsequent rows stored in buffer A are moved to buffer B (1710). The next 400 rows, in this example, are then stored in buffer A (1712). The rows of line scan image data in buffer A are then evaluated to determine if an end of the package has been detected (1714). If the end of the package is detected at (1716), prior rows in buffer A and the stored rows in buffer B are combined in grabber buffer D (1718). In one embodiment, the combined rows that form an image of the package 1725 are rotated and then placed in grabber buffer D. The rows that represent the image of the package 1725 are then analyzed. In one embodiment they are being mapped to determine select locations in the image of the package 1752 as discussed above.

The buffer flow diagram 1700 further deals with situations where packages are positioned on the conveyer belts 912 and 914 right next to each other such that the end of one package and the start of another package is hard to detect. Hence, if the end of a package is not detected at step (1716), the rows of pixels in the buffer B are moved to buffer C (1722). A select number of rows of line scan image data to compete an image of package are moved into buffer C from buffer A. The rows of line scan image data in buffer C is moved to grabber buffer D (1728) and is then analyzed at (1720). The remaining rows of line scan image data are moved from buffer A to buffer C (1726). The process then continues by storing rows of line scan image data in buffer A at step (1712) and continuing on. As further illustrated, once the analysis of the line scan image data that make up the image of the package 1752 is complete at step (1720) the process continues at step (1702). In embodiments, the line scan image data is coming from two cameras, the first camera with the 90 degree polarized filter and the second regular camera as described above. In order to keep the line scan image data from the first camera synchronized with the line scan image data taken at the same time from the second camera, the line scan image data from the second camera is buffered identically as the line scan data from the first camera is buffered in embodiments.

Figure 18:
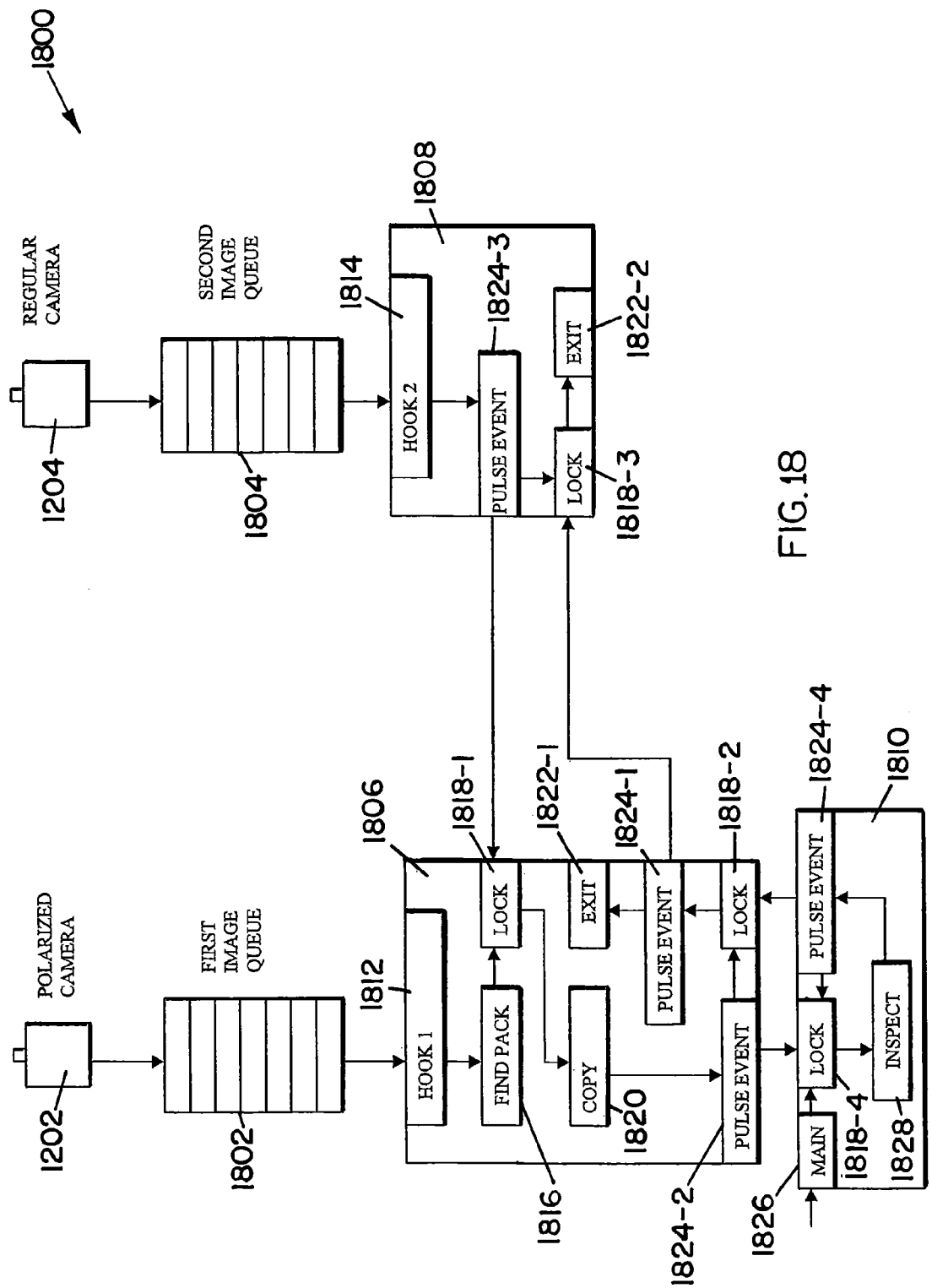
FIG. 18 illustrates a synchronization diagram of one embodiment of the present invention.

The system requires that the images formed by the line scam image data captured by the first camera 1202 and images formed by the line scan image data captured by the second camera 1204 remained synchronized so that the mapping set out in the first image of the first camera 1202 is applied the corresponding second image from the second camera 1204. A thread synchronization model diagram 1800 of a vision evaluation system of one embodiment is illustrated in FIG. 18. In one embodiment, the thread synchronization model 1800 is part of module 1404 implemented by processor 1401. The thread synchronization model 1800 keeps images in sequence and paired. As illustrated, the polarized camera 1202 (first camera 1202 providing polarized images) and the regular camera 1204 (second camera 1204 providing non-polarized images) provide respective images to respective first and second image queues 1802 and 1804 at a given frequency. Corresponding first and second images from the first and second cameras 1202 and 1204 are subject to a first processing thread 1806, a second processing thread 1808 and a main processing thread 1810 respectfully as illustrated in FIG. 18. In embodiments, the first camera 1202 and the second camera 1204 produce images at a fixed rate that must be processed in the order that they arrive. The processing time of the images are not constant and the processing time some times can take longer than the frame rate. When this happens the images start to accumulate in the respective image queues 1802 and 1804. The image queues 1802 and 1804 are part of the memory system 1406 of FIG. 14.

When images taken from the first camera leaves queue 1802 they enter hook one block 1812 of the first processing thread 1806 and when images taken by the second camera leaves queue 1804 they enter hook two block 1814 of the second processing thread 1808. In this embodiment, another image from the first camera 1202 cannot exit the first image queue 1802 until processing is finished at exit block 1822-1 of the first instruction set 1806. Similarly another image from the second camera 1204 cannot exit the second image queue 1804 until processing is finished at exit block 1822-2 of the second processing thread 1808. Referring to the first processing thread 1806, from the hook one block 1812 the first image is processed at the find pack block 1816. At the find pack block 1816 the first image from the first camera 1202 (which is a package in this embodiment) is analyzed to determine the location of a seal and to set out a map of the image as described above. Processing is locked at lock block 1818-1 of the first processing thread until the corresponding image from the second camera is available as indicated by pulse event block 1824-3 of the second processing thread 1808. Once the corresponding image is available from the second camera 1204, the first image from the first camera 1202 and the second corresponding image from the second camera 1204 are copied in the memory system 1406 at copy block 1820.

The second image from the second camera is then processed in the main processing thread 1810. The main block 1826 of the main processing thread 1810 is the entry point to the main processing thread 1810. The main block 1826 initializes and starts the main processing thread 1810. The processing begins when the pulse event block 1824-2 in the first processing thread 1806, in response from a signal from the copy block 1820, pulses a signal to the lock block 1818-4 in the main processing thread 1810. Once the inspection is done, the inspection block 1824 provides a signal to the pulse event block 1824-4 of the main processing thread 1810. The pulse event block 1824-4 in response, pulses a signal to lock block 1818-2 of the first processing thread 1806. Lock block 1818-2 in turn provides a signal to pulse event 1824-1 of the first processing thread 1806. Pulse event block 1824-1 then in turn signals exit block 1822-1 in the first processing thread to release the first camera thread and signals lock block 1818-3 in the second process thread to signal exit block 1822-2 of the second processing thread 1808 to release the second camera thread. The signals to exit block 1821-1 and 1821-2 terminate execution of the processing for related first and second images. The process then continues with the next first and second images from the respective first and second image queues 1802 and 1804.

As discussed above, the speed of the conveyer belts 912 and 914, the frequency of capturing line scan images, the speed of detecting the images in line scan image data and the speed of processing the images have to be coordinated so that all the processing is done before the package arrives at the rejection chute 1300. Hence, the speed of the conveyer belts 912 and 914, the speed of the processing and the frequency of capturing images are all interrelated and are all dependant on many factors including but not limited to the resolution of the line scan images (how much pixel data needs to be processed) and the length of the second conveyer 914. An, example of speeds used in one embodiment are a conveyer speed of 32 in/sec, a processing speed of 0.080 sec/image, a line scan image and a line scan image frequency rate of 4 images/sec.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A location determining apparatus, the apparatus, comprising:
   a light source configured to provide polarized backlight;
   a location camera having a lens positioned to receive the polarized backlight, the location camera being a line scan camera operating at a given frequency;
   at least one buffer to store line scan image data from the location camera;
   a polarizing filter that is orientated 90 degrees from the polarized backlight, the polarizing filter positioned between the lens of the location camera and the backlight; and
   a controller configured to determine the beginning of a package and an orientation of the package based on an analysis of the stored line scan data from the location camera in the at least one buffer.

2. The apparatus of claim 1, further comprising:
   the controller configured to determine select diffusion locations from the stored line scan image data.

3. The apparatus of claim 2, further comprising:
   an analyzing camera having a lens positioned near the lens of the location camera, the controller further configured to control the activation of both the location camera and the analyzing camera simultaneously, the control system further configured to analyze the select diffusion locations of the object in an image taken by the analyzing camera based on the determined select diffusion locations from the image of the location camera.

4. The apparatus of claim 3, wherein the controller is further configured to map out regions of the object based at least in part on at least one of the determined select diffusion locations of the object, the controller still further configured to analyze the object in the corresponding image taken by the analyzing camera based on the mapped out regions.

5. A vision evaluation system, the system comprising:
   a light source providing polarized back light;
   a first camera having a first lens positioned to image the polarized back light;
   a ninety degree polarized filter positioned between the first lens of the first camera and the light source, the ninety degree polarized filter being polarized 90 degrees from the polarized back light from the light source;
   a second camera having a second lens, the second lens positioned near the first lens of the first camera; and
   a control system coupled to control the first and second cameras to take simultaneous images at a given frequency, the control system further configured to determine the start of a package to be analyzed, the orientation of the package to be analyzed and locations to be analyzed based on image data from the first camera, the control system further configured to analyze the determined locations in associated image data from the second camera.

6. The system of claim 5, wherein the light source further comprises:
   a light assembly box having an opening;
   a light received in the light assembly box; and
   a polarized filter positioned between the light and the opening to the light assembly box.

7. The system of claim 5, further comprising:
   a zero degree polarized filter positioned between the second lens of the second camera and the polarized backlight, the zero degree polarized filter being polarized 0 degrees from the polarized back light.

8. The system of claim 5, further comprising:
   at least one conveyer belt system to move objects between the light source and the first and second cameras; and
   a conveyer belt speed determining device configured to determine the speed of the conveyer, the conveyer belt speed device in communication with the control system.

9. The system of claim 8, further comprising:
   a rejection chute to remove rejected objects from the at least one conveyer belt, the rejection chute in communication with the control system.

10. The system of claim 5, further comprising:
    the first and the second cameras being line scan cameras; and
    at least one buffer to store line scan image data from the first and second cameras.

11. A vision evaluation system, the system comprising:
    a first conveyer belt;
    a second conveyer belt positioned to receive packages from the first conveyer belt;
    a polarized light source positioned between the first and second conveyer belts such that packages passed from the first conveyer belt to the second conveyer belt are passed over the light source;
    a first line scan camera having a first lens with a ninety degree polarized filter that is polarized 90 degrees from the polarized light source, the first lens of the first camera positioned to receive light from the polarized light source;
    a second line scan camera having a second lens, the second lens of the second camera positioned near the first lens of the first camera;
    at least one buffer to store line scan image data from the first and second cameras;
    a control system coupled to activate the first and second cameras at a given frequency, the control system configured to store the line scan image data from the first and second cameras in the at least one buffer, the control system further configured to analyze package image data formed from the stored line scan image data in the at least one buffer; and
    a rejection chute in communication with the control system, the rejection chute positioned to separate packages that fail the analysis from the packages that pass the analysis from the second conveyer belt.

12. The system of claim 11, wherein the control system is further configured to determine locations of select areas to evaluate in package image data formed from line scan image data from the first camera and evaluate the select areas in associated package image data formed from the line scan image data from the second camera.

13. The system of claim 11, wherein the control system further comprises:
    a processor to process instructions and image data from the first and second cameras.

14. The system of claim 11, further comprising:
a conveyer belt speed determining device to determine the speed of the first and second conveyer belts, the conveyer belt speed determining device being in communication with the control system.

15. The system of claim 11, further comprising:
a camera housing, the first and second camera received in the camera housing;
a light box assembly, the polarized light source received in the light box assembly; and
a stand alone image assembly coupled to the camera housing and the light box assembly.

16. The system of claim 15, further comprising:
an air knife assembly coupled to the stand alone image assembly to remove debris from the light box assembly.

17. The system of claim 11, further comprising:
a zero degree polarized filter for the second camera lens that is oriented at 0 degrees with regarding to the polarized light source.

18. The system of claim 11, further comprising:
a product guide coupled to the rejection chute to pass packages that pass the analysis when the rejection chute is not activated; and
a pneumatic cylinder coupled to raise the rejection chute in response to a signal from the control system, the raised rejection chute providing a path for the packages that fail the analysis.

19. The system of claim 11, further comprising:
at least one input in communication with the control system to provide at least one of instruction and adjustments in analysis instructions; and
at least one output in communication with the control system to provide at least one of an indication of the current setup of the control system and the results of the analyzes of packages.

20. A method of evaluating transparent product packages, the method comprising:
passing packages between a polarized light source and first and second cameras, the first camera having a polarized filter that is polarized 90 degrees from the polarized light source;
capturing line scan image data with the first and second cameras at a given frequency, wherein the frequency of taking the line scan images by the first and second cameras is based at least in part on the speed that the packages pass between the polarized light source and the first and second cameras;
determining the start of a package and an orientation of the package based on captured line scan image data;
analyzing line scan image data that make up package images from the first camera to determine select locations on the package images to evaluate; and
analyzing the determined select locations on associated package images from the line scan image data from the second camera to determine if packages pass inspection.

21. The method of claim 20, further comprising:
calibrating the line scan image data of the first camera with the line scan image data of the second camera.

22. The method of claim 21, wherein calibrating the line scan image data of the first camera with the line scan image data of the second camera further comprises:
capturing an image with the first and second cameras;
determining differences between reference points between the image from the first camera and the image from the second camera; and
based on the differences, applying an interpolation algorithm on the line scan image data from one of the first and second cameras to calibrate the line scan image data between the first and second cameras.

23. The method of claim 20, further comprising:
monitoring the speed of at least one conveyer belt passing the packages.

24. The method of claim 20, further comprising:
storing the line scan image data from the first and second camera in at least one buffer; and
forming images of packages captured by the first camera and the second camera from the line scan image data stored in the at least one buffer.

25. The method of claim 24, further comprising:
designating a reference point on each of the formed images from the first camera;
creating an X and Y coordinate system based on the reference point on each of the formed images from the first camera;
determining an angle of rotation of the X and Y coordinate system in relation to the reference point on each image of the formed images from the first camera; and
mapping out the select locations to be analyzed in the X and Y coordinate system of each of the formed images of the first camera.

26. The method of claim 25, further comprising:
determining a corresponding reference point on each of the formed images from the second camera, wherein each formed image from the second camera is associated with each formed image from the first camera whose line scan image data was captured at the same time;
applying the X and Y coordinate system with the angle of rotation to the second images using the determined reference points; and
analyzing the mapped out areas of the X and Y coordinate system in the second images.

27. The method of claim 24, further comprising:
placing a select number of rows of line scan data in a first buffer;
determining if any of the rows of line scan data in the first buffer indicate the beginning of a package;
when a row of line scan data in the first buffer indicates the beginning of the package, moving the row and subsequent rows in the first buffer to a second buffer; and
when none of the rows in the first buffer indicate the beginning of a package, storing a new select number of rows of line scan data in the first buffer.

28. The method of claim 27, further comprising:
determining if any rows of line scan data in the first buffer indicate the end of a package;
when a row of the line scan data in the first buffer indicates the end of a package, combining prior rows of line scan data in the first buffer with the stored rows in the second buffer to form an image of the package; and
when a row of the line scan data in the first buffer does not indicate the end of a package, moving the stored rows of line scan data in the second buffer into a third buffer and moving the stored rows of line scan data in the first buffer to the second buffer.

29. The method of claim 20, wherein the analysis of the determined select locations is a pixel analysis.

30. The method of claim 20, further comprising:
tracking associated package images from the first and second cameras taken simultaneously; and
synchronizing the associated package images from the first and second cameras taken simultaneously.

31. The method of claim 20, wherein analyzing the determined select locations on associated package images from the line scan image data from the second camera to determine if packages pass inspection includes at least one of analyzing the integrity of seals, analyzing for the presence of an absorbing pad and analyzing for the presence of a product.

32. The method of claim 21, wherein the analyzing does not occur until a package is detected.

33. A method of processing transparent packages, the method comprising:
- passing polarized back light through a transparent package;
- imaging the package through a filter that is polarized 90 degrees from the polarized back light;
- determining the beginning of a package and the orientation of the package via the imaging through the filter that is polarized 90 degrees from the polarized back light;
- locating areas of the package that are lighter in a first image from the imaging, wherein the lighter areas are due to diffusion of the polarized back light caused by thermal seals in the package; and
- analyzing the thermal seals in a second different image based on the located areas in the first image.

* * * * *